United States Patent
Wu et al.

[11] Patent Number: 6,129,742
[45] Date of Patent: Oct. 10, 2000

[54] THIN FILM RESISTOR FOR USE IN MEDICAL DEVICES AND METHOD OF MAKING SAME

[75] Inventors: Fan Wu, Gilbert; Allen W. McLaurin; Doug G. Managhan, both of Tempe; Kirk Henson, Mesa, all of Ariz.

[73] Assignee: Medtronic, Inc., Minneapolis, Minn.

[21] Appl. No.: 09/281,910

[22] Filed: Mar. 31, 1999

[51] Int. Cl.[7] .................................................. A61N 1/00
[52] U.S. Cl. ..................................................... 607/1
[58] Field of Search ................................ 128/899; 607/1, 607/5, 116; 600/509

[56] References Cited

U.S. PATENT DOCUMENTS

| | | |
|---|---|---|
| 4,379,459 | 4/1983 | Stein . |
| 4,476,868 | 10/1984 | Thompson . |
| 4,510,178 | 4/1985 | Paulson et al. . |
| 4,556,063 | 12/1985 | Thompson et al. . |
| 4,821,723 | 4/1989 | Baker et al. . |
| 5,127,404 | 7/1992 | Wyborny et al. . |
| 5,131,388 | 7/1992 | Pless . |
| 5,144,949 | 9/1992 | Olson . |
| 5,158,078 | 10/1992 | Bennett et al. . |
| 5,199,428 | 4/1993 | Obel et al. . |
| 5,207,218 | 5/1993 | Carpentier et al. . |
| 5,312,453 | 5/1994 | Shelton et al. . |
| 5,314,430 | 5/1994 | Bardy . |
| 5,330,507 | 7/1994 | Schwartz . |
| 5,331,966 | 7/1994 | Bennett et al. . |
| 5,354,316 | 10/1994 | Keimel . |
| 5,468,672 | 11/1995 | Rosvold . |
| 5,545,186 | 8/1996 | Olson et al. . |

OTHER PUBLICATIONS

Berry, R.W., *Thin Film Technology* (1979).
Schroeder, D.K., *Semiconductor Material and Device Characterization* (1998).

Primary Examiner—William E. Kamm
Attorney, Agent, or Firm—Thomas F. Woods; Harold R. Patton

[57] ABSTRACT

A method for forming a thin film resistor includes providing a sputter target having one or more silicon containing components and chromium diboride. For example, the one or more silicon containing components may include silicon and/or silicon carbide. The resistor film is then sputter deposited on a surface using a nitrogen containing sputter gas. The resistor material generally is sputtered to a thickness in the range of about 125 Å to about 500 Å while maintaining a desirable sheet resistance. The resistor film may be used in one or more electrical circuits, such as in an implantable medical device.

80 Claims, 13 Drawing Sheets

THIN FILM RESISTOR FOR USE IN MEDICAL DEVICES AND METHOD OF MAKING SAME

FIELD OF THE INVENTION

The present invention relates to resistors, e.g., resistors used in electronic circuits for medical devices. More particularly, the present invention pertains to thin film resistors having a composition including one or more silicon containing components and chromium diboride.

BACKGROUND OF THE INVENTION

Resistors are commonly used in electronic circuits to inhibit the flow of electric current. Frequently, thin film resistors are combined with other semiconductor structures to make extremely compact, yet complex, circuitry. For example, thin film resistors may be used as part of an individual device, e.g., a resistor in a power transistor, or may be used in connection with a multiple number of other semiconductor devices to form complex integrated circuits and/or hybrids. For example, such thin film resistors may be used as current limiting and load resistors in amplifiers, as a part of resistor arrays, etc.

Thin film resistors generally consist of a thin film of resistive material deposited, such as by sputter deposition, on a layer of insulative material of a substrate. End contacts are formed relative to the resistive material. The end contacts or interconnections are then connected to other circuit components in a conventional manner.

Thin film resistors are generally characterized in terms of their sheet resistance and their temperature dependence. Sheet resistance is expressed in resistance per unit area (e.g., ohms per square ($\Omega$/sq)) and is equal to the bulk resistivity divided by the film thickness. Sheet resistance is a material property and is not dependent on the topology of a particular resistor. The resistance of a specific resistor is obtained by multiplying the sheet resistance by the ratio of the resistor length to width.

The temperature dependence of thin film resistors is described in terms of the temperature coefficient of resistance (TCR) which reflects the slope of the resistivity versus temperature curve. In other words, the TCR reflects the fractional change in resistance per unit change in temperature. Generally, it is expressed in parts per million change per degree centigrade (ppm/° C.). The TCR may be positive or negative. Conventional film resistor materials typically have TCRs in the range of a few hundred to a few thousand ppm/° C., positive or negative.

There are various criteria by which the quality of thin film resistors are evaluated. For example, it is generally desirable that a thin film resistor have a minimum thickness. When a thin film resistor is too thin, it may be unable to handle relatively large current densities during operation. Further, it is typically desirable that a thin film resistor have uniform thickness and properties to ensure consistency and stability. Also, it is generally desirable that thin film resistors have a target or intended sheet resistance. Yet further, it is normally desirable that thin film resistors have a very low TCR, or at least a TCR that is suitably matched to a particular application. For example, it may be desirable to have a TCR that is either positive or negative, or have a TCR that is zero. For example, a thin film resistor with a zero TCR does not vary in resistance as the temperature changes.

Various resistive materials have been used to form thin film resistors. For example, chromium diboride, silicon chromide, nickel chromium, etc. have been used to fabricate thin film resistors. However, although such resistive materials may be used to fabricate thin film resistors having relatively low sheet resistances, e.g., less than about 1.5 k$\Omega$/sq, these materials and others have not generally been suitable for attaining sheet resistances that are relatively high, e.g., 1.5 k$\Omega$/sq or higher. Particularly, such resistive materials have not been suitable for forming relatively high sheet resistance values due to the inherent properties of the resistive materials. For example, to attain relatively high sheet resistance using such resistive materials, the thickness of the thin film resistor formed is undesirably thin, e.g., less than 100 Å. Not only are such film resistors undesirably thin and unable to handle relatively high current densities in operation, as previously described, but it is difficult to reproducibly form such undesirably thin film resistors. Further, uniformity of such thin resistors is problematic.

Relatively high sheet resistance characteristics are particularly important in various product areas. For example, electronic devices, which operate at relatively low power, generally require the use of thin film resistors with high sheet resistance. In particular, implantable medical devices generally operate at such lower power requirements and require high sheet resistance thin film resistors. Further, high sheet resistance also provides for a beneficial reduction in the size of a resistor.

Further, commonly used resistive materials do not provide for thin film resistors that have a TCR that is suitably controllable. For example, if a zero TCR is even achievable, it is generally zero TCR over only a very small temperature range. Further, for example, thin film resistors formed of such conventional resistive materials generally have a TCR that is not temperature independent. A temperature independent TCR is one in which the resistivity is a linear function of temperature over the temperature range of interest, e.g., −55° C. to about +125° C. For example, a parabolic variation of resistivity with temperature does not have a temperature independent TCR.

As such, thin film resistors having high sheet resistance are desired. In addition, a thin film resistor having a controllable or adjustable TCR, e.g., a zero TCR or a TCR that is temperature independent, are important for various applications, e.g., implantable medical device operation.

Table 1 below lists U.S. patents relating to thin film resistor fabrication techniques:

TABLE 1

| U.S. Pat. No. | Inventor(s) | Issue Date |
| --- | --- | --- |
| 4,510,178 | Paulson, et al. | 9 April 1985 |
| 5,468,672 | Rosvold | 21 November 1995 |

Further, other thin film resistors are described in the book entitled *Thin Film Technology* by Robert W. Berry (1979).

All references listed in Table 1, and elsewhere herein, are incorporated by reference in their respective entireties. As those of ordinary skill in the art will appreciate readily upon reading the Summary of the Invention, Detailed Description of the Embodiments, and claims set forth below, at least some of the devices and methods disclosed in the references of Table 1 and elsewhere herein may be modified advantageously by using the teachings of the present invention. However, the listing of any such references in Table 1, or elsewhere herein, is by no means an indication that such references are prior art to the present invention.

SUMMARY OF THE INVENTION

The present invention has certain objects. That is, various embodiments of the present invention provide solutions to one or more problems existing in the prior art with respect to thin film resistors and methods for making such thin film resistors. One of such problems involves the lack of ability to attain desirably high sheet resistance characteristics for a thin film resistor. Further, for example, other problems include the lack of uniformity with respect to thin film resistors while attaining high sheet resistance characteristics, the inability to control deposition processes for thin film resistors to attain such high sheet resistance characteristics, the inability to achieve a zero temperature coefficient of resistance for resistive material forming the thin film resistor, the inability to suitably provide for an adjustable temperature coefficient of resistance for the thin film resistor material, the complexity of various deposition processes used to form thin film resistors, and the inability to attain a high sheet resistance for a thin film resistor useable in low power implantable medical devices. Further, the reproducibility of thin film resistors, in addition to the uniformity of such thin film resistors, is also lacking when using conventional thin film resistor processing techniques.

In comparison to known techniques for providing thin film resistors and methods for providing such thin film resistors, various embodiments of the present invention may provide one or more of the following advantages. For example, zero temperature coefficient of resistance may be attained. A temperature coefficient of resistance may be adjusted by adjusting process parameters, such as sputter target composition, sputtering atmosphere, anneal temperature, etc. Further, the sheet resistance of the thin film resistor can be adjusted by adjusting the process parameters. Likewise, various embodiments of the present invention provide for a reproducible process for providing a uniform thin film resistor. Further, the present invention has the advantage of being a fairly simple fabrication process. In addition, with an adjustable TCR and high sheet resistance being possible according to the embodiments of the present invention, thin film resistors for low power applications, e.g., implantable medical devices such as pacemakers, may be provided.

Some embodiments of the present invention include one or more of the following features: a resistor, such as for one or more electrical circuits of a medical device, wherein the resistor composition includes silicon, silicon carbide, and chromium diboride; a medical device or other low power device including one or more electrical circuits having a resistor that includes at least one silicon containing component and chromium diboride with the resistor having a thickness in the range of about 125 Å to about 500 Å; such a resistor having a thickness greater than about 300 Å; a resistor having a temperature coefficient of resistance in the range of about −3000 ppm/° C. to about +400 ppm/° C.; a resistor having a zero temperature coefficient of resistance; a resistor having a sheet resistance in the range of about 500Ω/sq to about 100 kΩ/sq.

Still further, some embodiments of the present invention include one or more of the following features: providing a sputter target in a chamber wherein the sputter target includes at least one silicon containing component and chromium diboride; sputter depositing a resistive material onto a substrate surface using a nitrogen containing sputter gas to a thickness in the range of about 125 Å to about 500 Å; performing an anneal of deposited resistive material; annealing deposited resistive material in an anneal atmosphere comprising at least nitrogen; annealing deposited resistive material in an anneal atmosphere of nitrogen and hydrogen; adjusting the temperature coefficient of resistance of the resistive material by controlling the anneal atmosphere, anneal temperature, and/or the sputtering atmosphere (e.g., concentration of nitrogen in the atmosphere); adjusting the sheet resistance of resistive material by controlling the anneal atmosphere, anneal temperature, and/or the sputtering atmosphere; providing a sputter target which includes silicon, silicon carbide, and chromium diboride; sputter depositing resistive material using a sputter gas comprising nitrogen and argon; and forming a resistor by exposing a substrate assembly surface to one or more sources of silicon, silicon carbide, chromium diboride, and nitrogen.

The above summary of the present invention is not intended to describe each embodiment or every implementation of the present invention. Advantages, together with a more complete understanding of the invention will become apparent and appreciated by referring to the following detailed description and claims taken in conjunction with the accompanying drawings.

DETAILED DESCRIPTION OF THE EMBODIMENTS

Figure 1:
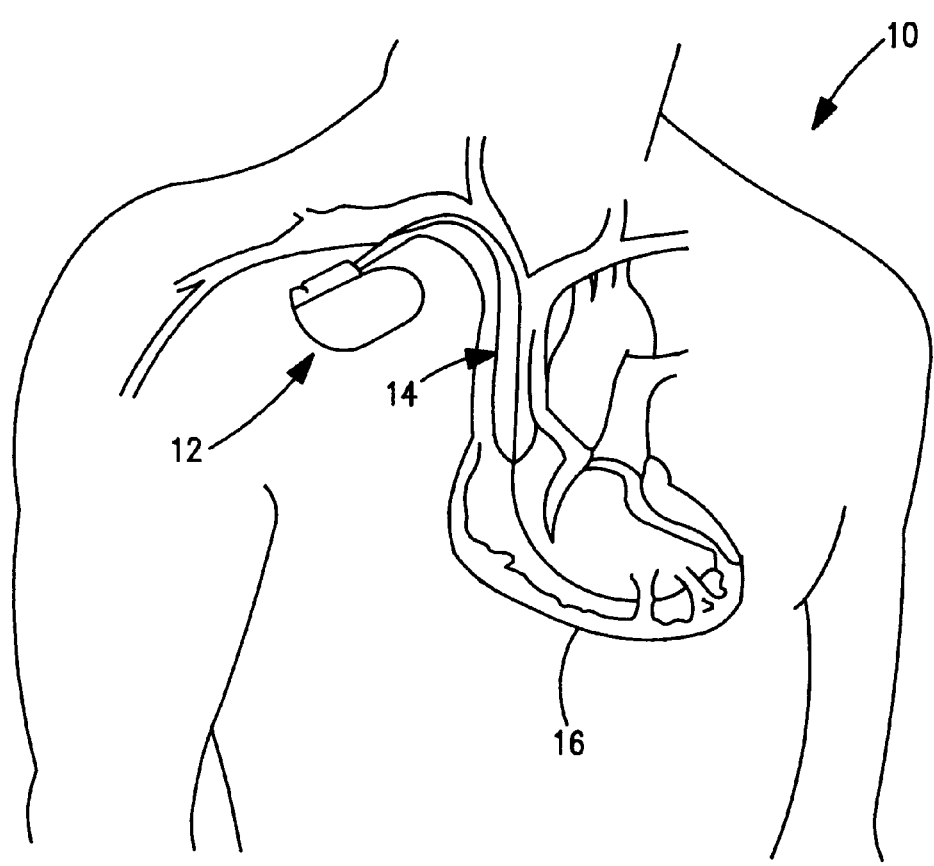
FIG. 1 is a diagram illustrating an implantable medical device in a body, wherein the implantable medical device includes one or more electrical circuits having at least one thin film resistor formed according to the present invention.

FIG. 1 is a simplified schematic view of an implantable medical device 12 including one or more electrical circuits having at least one thin film resistor formed according to the present invention. The implantable medical device 12 is implanted in a body 10 near a human heart 16. Implanted medical device 12 is electrically connected to the heart by leads 14. In the case where the implanted medical device 12 is a pacemaker, the leads 14 are pacing and sensing leads connected to the heart 16 from the implanted medical device 12. Such leads sense electrical signals attendant to the depolarization and repolarization of the heart 16 and provide pacing pulses for causing depolarization of cardiac tissue in the vicinity of the distal ends thereof. Implantable medical device 12 may be any implantable cardiac pacemaker such as those disclosed in U.S. Pat. No. 5,158,078 to Bennett et al.; U.S. Pat. No. 5,312,453 to Shelton et al.; or U.S. Pat. No. 5,144,949 to Olson.

Implantable medical device 12 may also be a pacemaker-cardioverter-defibrillator (PCD) corresponding to any of the various commercially-available implantable PCDs. For example, the present invention may be practiced in conjunction with PCDs such as those described in U.S. Pat. No. 5,545,186 to Olson et al.; U.S. Pat. No. 5,354,316 to Keimel; U.S. Pat. No. 5,314,430 to Bardy; U.S. Pat. No. 5,131,388 to Pless; or U.S. Pat. No. 4,821,723 to Baker, et al.

Alternatively, implantable medical device 12 may be an implantable nerve stimulator or muscle stimulator such as that disclosed in U.S. Pat. No. 5,199,428 to Obel et al.; U.S. Pat. No. 5,207,218 to Carpentier et al.; U.S. Pat. No. 5,330,507 to Schwartz; or an implantable monitoring device such as that disclosed in U.S. Pat. No. 5,331,966 issued to Bennett et al.

Further, for example, the implanted medical device 12 may be a defibrillator, a cardioverter-defibrillator, a brain stimulator, a gastric stimulator, a drug pump, a hemodynamic monitoring device, or any other implantable device that would benefit from thin film resistors formed as described herein. Therefore, the present invention is believed to find wide application in any form of implantable medical device. As such, a description herein making reference to any particular medical device is not to be taken as a limitation of the type of medical device which can benefit from and which can employ one or more thin film resistors as described herein.

Further, although the present invention is particularly described with reference to use of thin film resistors in implantable medical devices, the present invention is in no manner limited to such applications. For example, the present invention may be used in any electronic application where a thin film resistor as described herein is beneficial as would be readily apparent to one skilled in the art from the description herein. For example, the thin film resistor as described herein may be used in a power management circuit of a portable personal computer, a resistor array of a low power device such as a high voltage resistor array for a tachyarrhythmia management device, a sense amplifier circuit for a pacemaker, or any other application as would readily be apparent to one skilled in the art from the description herein.

In general, the implantable medical device 12 may include a hermetically sealed enclosure that may include various elements such as an electrochemical cell (e.g., a lithium battery), circuitry that controls device operations and records rhythmic EGM episodes, telemetry transceiver antenna and circuit that receives downlink telemetry commands from and transmits stored data in a telemetry uplink to an external programmer, etc. Generally, the medical device is implemented with a microprocessor-based architecture. However, electronic features and operations of the implantable medical device may be implemented in discrete logic or as a microcomputer-based system, as would be readily apparent to one skilled in the art.

Figure 2:
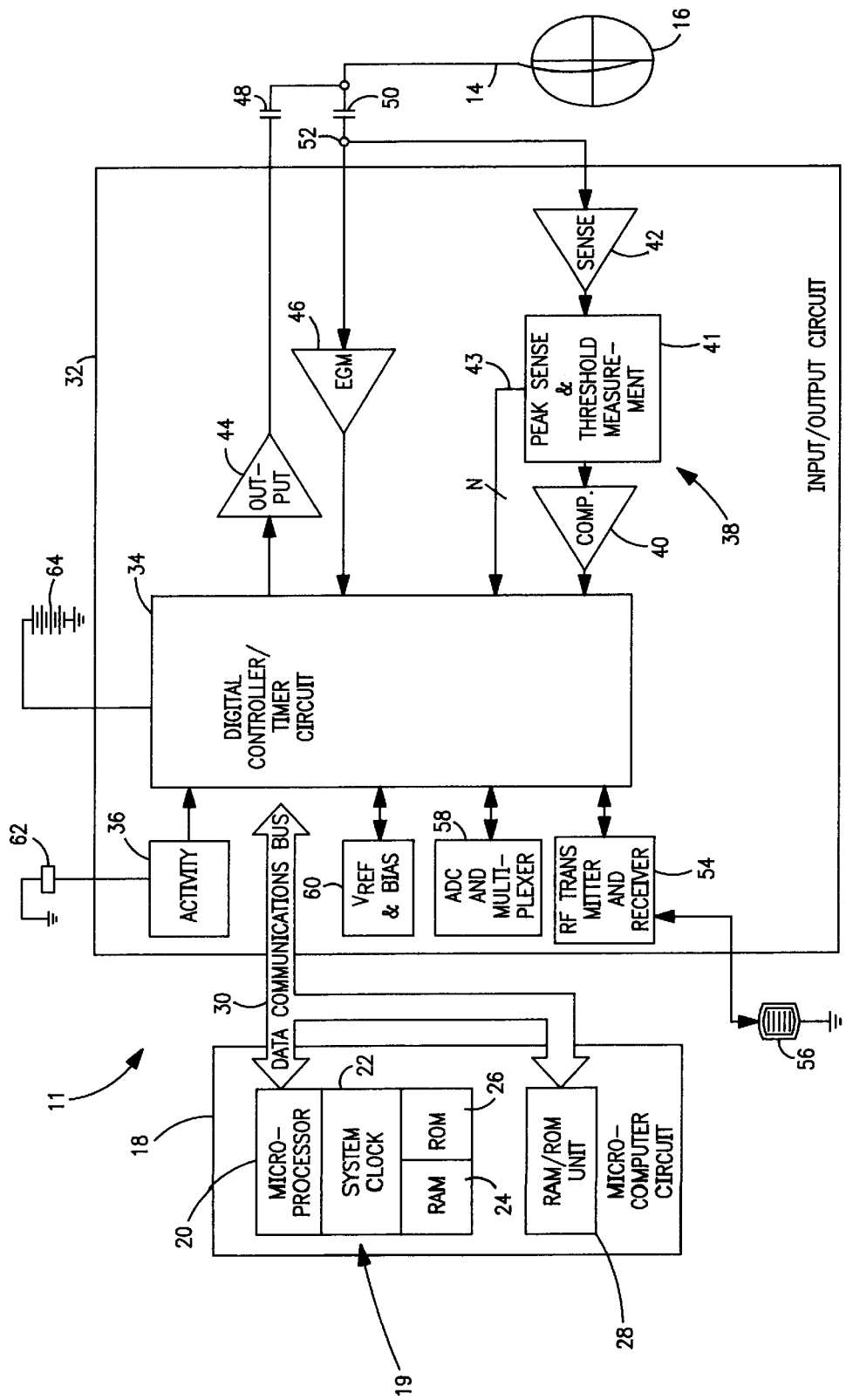
FIG. 2 is a general block diagram of circuitry of one embodiment of the implantable medical device of FIG. 1 including one or more electrical circuits having at least one thin film resistor formed according to the present invention.

FIG. 2 shows a block diagram illustrating components of a pacemaker 11 in accordance with one embodiment of the present invention where pacemaker 11 has at least one electrical circuit that is formed including one or more thin film resistors according to the present invention. In the illustrative embodiment shown in FIG. 2, the pacemaker 11 is preferably programmable by means of an external programming unit (not shown). One such programmer suitable for the purposes of the present invention is the commercially-available Medtronic Model 9790 programmer. The programmer is a microprocessor device which provides a series of encoded signals to pacemaker 11 by means of a programming head which transmits radiofrequency (RF) encoded signals to pacemaker 11 according to a telemetry system such as, for example, that described in U.S. Pat. No. 5,127,404 to Wybomy et al. It is to be understood, however, that any programming methodology may be employed so long as the desired information is transmitted to and from the pacemaker 11.

Pacemaker 11 illustratively shown in FIG. 2 is electrically coupled to the patient's heart 16 by lead 14. Lead 14 is coupled to a node 52 in the circuitry of pacemaker 11 through input capacitor 50. In the presently disclosed embodiment, an activity sensor 62 provides a sensor output to an activity circuit 36 of input/output circuit 32. Input/output circuit 32 also contains circuits for interfacing to heart 16, antenna 56, and contains circuits 44 for application of stimulating pulses to heart 16 to control its rate under control of software-implemented algorithms in microcomputer unit 18.

Microcomputer unit 18 preferably comprises on-board circuit 19 that includes microprocessor 20, system clock 22, and on-board random access memory (RAM) 24 and read-only memory (ROM) 26. In this illustrative embodiment, off-board circuit 28 comprises a RAM/ROM unit. On-board circuit 19 and off-board circuit 28 are each coupled by a communication bus 30 to digital controller/timer circuit 34.

The electrical components shown in FIG. 2 are powered by an appropriate implantable battery power source 64 in accordance with common practice in the art. For the sake of clarity, the coupling of battery power to the various components of pacemaker 11 is not shown in the figures.

Antenna 56 is connected to input/output circuit 32 to permit uplink/downlink telemetry through RF transmitter and receiver unit 54. Unit 54 may correspond to the telemetry and program logic disclosed in U.S. Pat. No. 4,556,063 issued to Thompson et al. or to that disclosed in the above-referenced Wybomy et al. patent.

$V_{REF}$ and bias circuit 60 generates a stable voltage reference and bias currents for circuits of input/output circuit 32. Analog to digital converter (ADC) and multiplexer unit 58 digitizes analog signals and voltages to provide "real-time" telemetry intracardiac signals and battery end-of-life (EOL) replacement function.

Operating commands for controlling the timing of pacemaker 11 are coupled by bus 30 to digital controller/timer circuit 34, where digital timers and counters establish the overall escape interval of the pacemaker as well as various refractory, blanking, and other timing windows for controlling the operation of the peripheral components disposed within input/output circuit 32. Digital controller/timer circuit 34 is preferably coupled to sense circuitry 38, including sense amplifier 42, peak sense and threshold measurement unit 41, and comparator/threshold detector 40. Sense amplifier 42 amplifies sensed electrocardiac signals and provides an amplified signal to peak sense and threshold measurement circuitry 41. Circuitry 41 in turn provides an indication of peak sensed voltages and measured sense amplifier threshold voltages on path 43 to digital controller/timer circuit 34. An amplified sense amplifier signal is also provided to comparator/threshold detector 40. Sense amplifier 42 may, for example, correspond to that disclosed in U.S. Pat. No. 4,379,459 to Stein. Such an amplifier may include one or more thin film resistors formed according to the present invention.

Circuit 34 is further preferably coupled to electrogram (EGM) amplifier 46 for receiving amplified process signals sensed by an electrode disposed on lead 14. The electrogram signal provided by EGM amplifier 46 is employed when the implanted device is being interrogated by an external programmer (not shown) to transmit by uplink telemetry a representation of an analog electrogram of the patient's electrical heart activity. Such functionality is, for example, shown in U.S. Pat. No. 4,556,063 to Thompson et al.

Output pulse generator 44 provides pulsing stimuli to the patient's heart 16 through coupling capacitor 48 in response to a pacing trigger signal provided by digital controller/timer circuit 34. Output amplifier 44, for example, may correspond generally to the output amplifier disclosed in U.S. Pat. No. 4,476,868 to Thompson.

According to the present invention, an implantable medical device 12, such as that shown in the illustrative embodiment of the pacemaker 11 in FIG. 2, includes one or more electrical circuits having at least one thin film resistor, e.g., a resistor network or array, employed therein. Such thin film resistors and methods of forming such resistors shall be described further in detail below with reference to FIGS. 3–11.

Figure 3A:
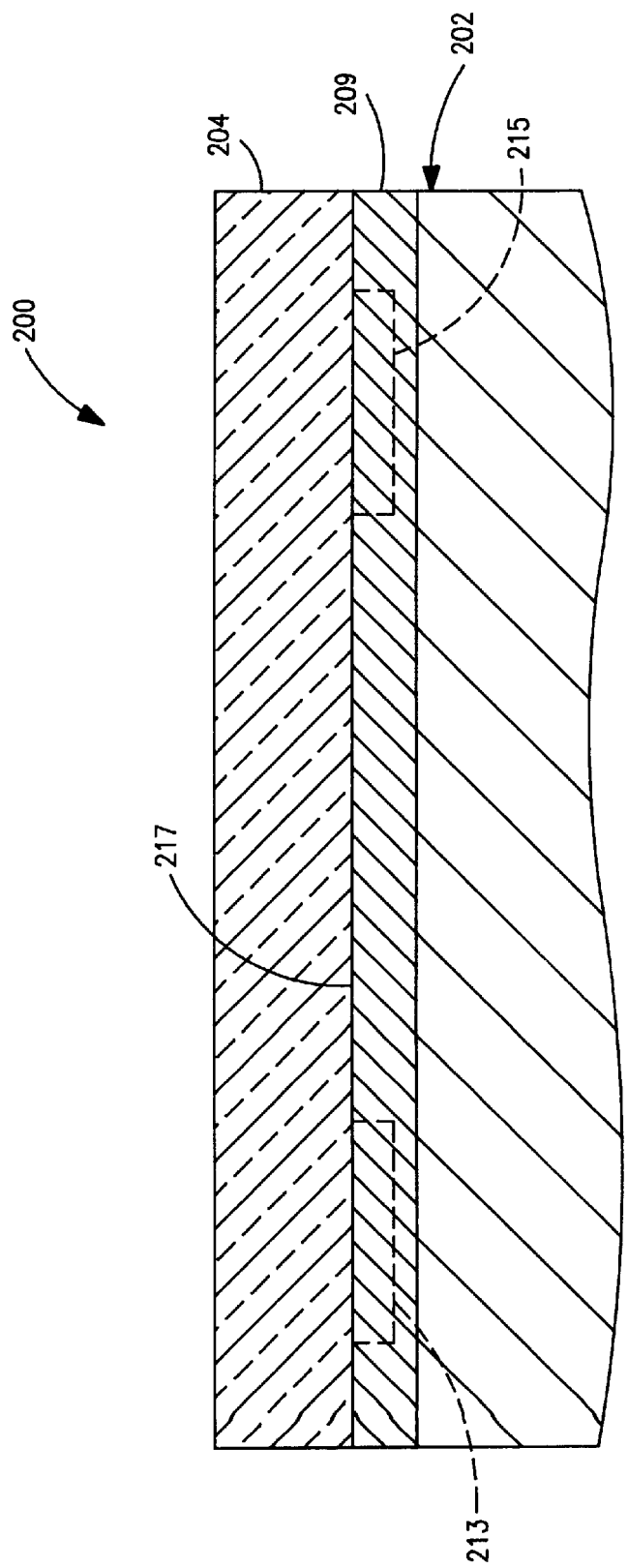
FIGS. 3A–3C are cross-section views illustrating the method of forming a thin film resistor according to the present invention.

FIG. 3A is a cross-section of a semiconductor structure 200. The semiconductor structure 200 includes a substrate assembly 202 and a thin film resistor layer 204 formed on the substrate assembly 202 according to the deposition method further described below.

Substrate assembly 202 as used herein may refer to either a semiconductor substrate such as the base semiconductor layer, e.g., the lowest layer of the silicon material on a wafer, or a silicon layer deposited on another material, such as silicon on sapphire, with the semiconductor substrate having an insulative layer 209 formed thereon. The insulative layer 209 has an upper surface 217 upon which the thin film resistor layer 204 is formed. Further, the semiconductor substrate assembly may include one or more layers below the insulative layer 209 and the insulative layer 209 may be formed of one or more layers. When reference is made to the substrate assembly 202 in the following description, various process steps may have been previously used to form or define regions, junctions, various structures, or features and openings such as vias, contact openings, high aspect ratios, etc. in the one or more layers forming the substrate assembly 202. Although the present invention is described with respect to the substrate assembly being a semiconductor structure, the thin film resistor may be formed on any substrate material, e.g., ceramic, printed circuit board materials, etc. The present invention is not limited to use of the thin film resistor material described herein with only semiconductor structures.

However, the thin film resistor layer 204 is preferably formed over at least one region of insulative material used to isolate the thin film resistor to be formed from other conductive structures, layers, regions, etc. Therefore, preferably, at least a portion of surface 217 over which the thin film resistor material is formed is an insulative material.

The insulative layer 209, including surface 217, may be any insulative material such as silicon nitride or any oxide material. For example, the insulative layer 209 and surface 217 thereof may be formed of silicon dioxide, tetraorthosilicate glass (TEOS), borophosphosilicate glass (BPSG), phosphosilicate glass (PSG), thermal oxide, or any other insulative material.

As shown in FIG. 3A, substrate assembly 202 may include conductive elements 213 or 215 shown in dashed lines for interconnection of a thin film resistor formed thereover. However, generally, the resistor is formed over an insulative layer 217 without any conductive portions at the surface thereof. Interconnection of the thin film resistors is generally provided by formation of conductive elements, such as contacts 206, 208, on the formed thin film resistor as shown in FIG. 3C, as opposed to below the thin film resistor.

The thin film resistor layer 204 is formed on the insulative surface 217 of insulative layer 209. The thin film resistor layer 204 is preferably formed of chromium diboride ($CrB_2$) and at least one silicon component. Preferably, the at least one silicon component includes silicon (Si) and silicon carbide (SiC). Further, the thin film resistor layer 204 may include nitrogen. As such, preferably, the elements which form the thin film resistor layer 204 include boron, carbon, nitrogen, silicon, and chromium. Further, oxygen may be present in the film, as will be further described below with respect to Example 11 which shows the atomic concentrations of elements present in certain resistor samples. Likewise, hydrogen may also be present in the thin film resistor depending upon processing conditions.

However, according to one embodiment of the present invention, a composition of the thin film resistor layer 204 which provides the advantages as described herein preferably includes silicon, silicon carbide, chromium diboride, and nitrogen. The other elements present, except for possibly hydrogen, do not appear to have a significant effect on the characteristics of the thin film resistor layer 204. The advantageous characteristics of a thin film resistor having such a composition are further described below.

Preferably, as shown in FIG. 3A, the thin film resistor layer 204 is formed on the insulative surface 217 to a thickness in the range of about 125 Å to about 500 Å. More preferably, the thickness of the resistor film 204 is greater than 300 Å. Films having a thickness over 125 Å, and preferably over 300 Å, provide the ability to more easily control the deposition process for forming the thin film resistor layer 204. As will be described further below, the process of forming thin film resistor layer 204 can be controlled to adjust the characteristics of layer 204. Preferably, the temperature coefficient of resistance (TCR) can be adjusted in the range from about −3000 ppm/° C. to about +400 ppm/° C. More preferably, the TCR can be adjusted in the range from about −300 ppm/° C. to about +200 ppm/° C. The process as described below may also be adjusted such that a zero TCR for the thin film resistor layer 204 can be attained. Further, preferably, sheet resistance for the thin film resistor layer 204 can be adjusted in a range from about 0.5 kΩ/sq to about 100 kΩ/sq.

Figure 3B:
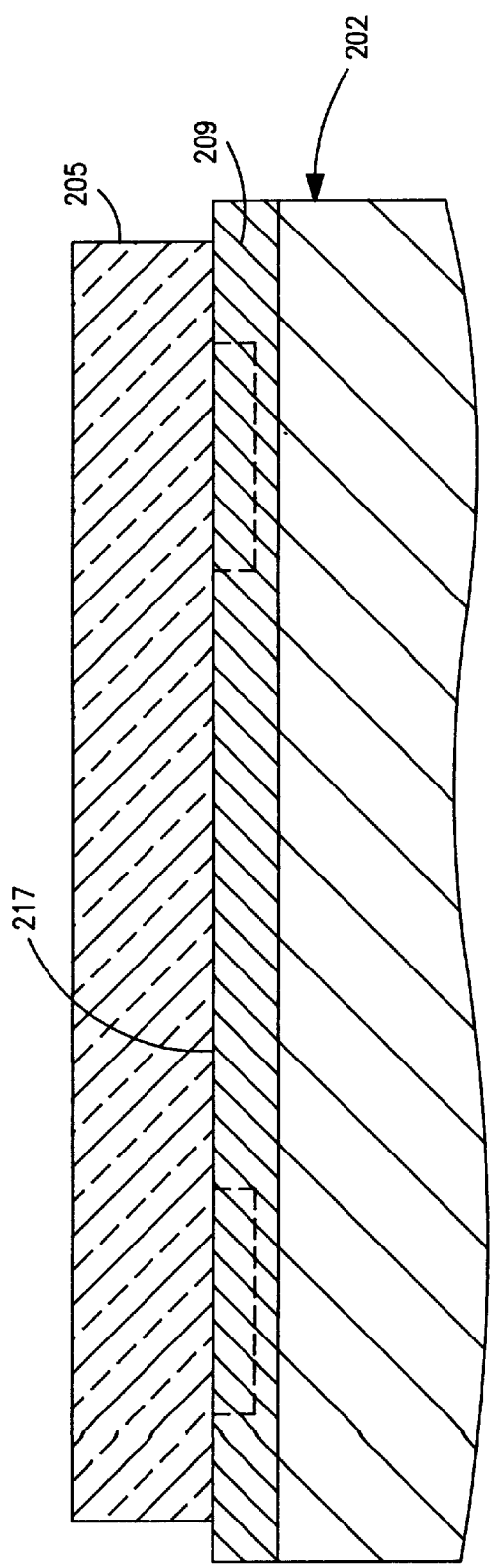
Figure 3C:
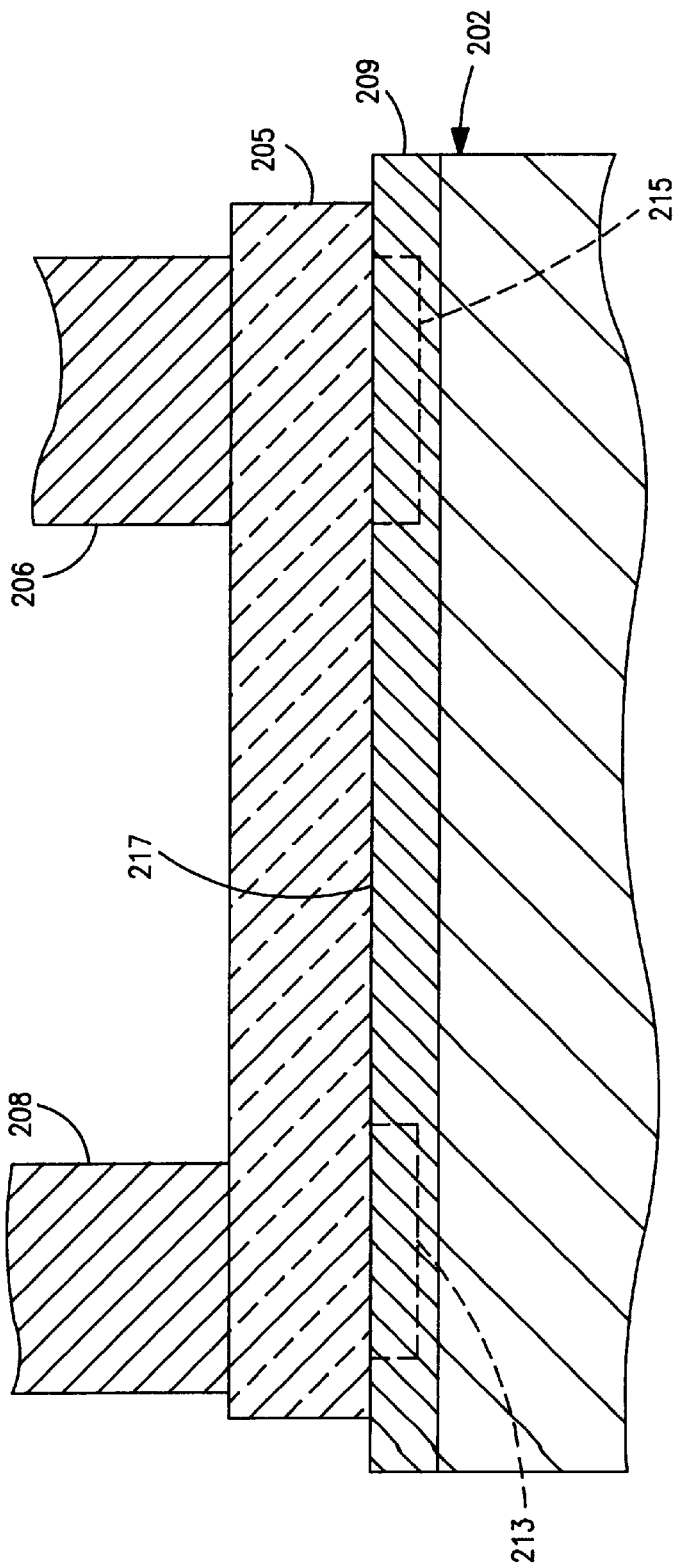

After the thin film resistor layer 204 is formed on the substrate assembly 202 according to the present invention, thin film resistor layer 204 may be patterned to produce a desired thin film resistor 205, e.g., resistor material of appropriate width and length to give the desired resistance value, as shown in FIG. 3B. Such patterning may be accomplished using various mask layers and/or etchants as would be known to one skilled in the art. For example, the thin film resistor layer 204 may be patterned using a layer of photoresist that is exposed and developed using photolithography methods that are well known in the art. The thin film resistor layer 204 may be then etched to remove exposed regions of the resistor layer 204 leaving the desired structure for the thin film resistor 205.

Etchants for etching a thin film resistor layer 204 formed according to the present invention generally include etchants conventionally used for etching conductive materials. For example, a suitable etchant may include a combination of $BCl_3$, $Cl_2$, He, and $SF_6$.

One skilled in the art will recognize that the thin film resistor layer 204 may be patterned before or after thermal treatment or annealing steps which are performed as further described below. Further, one skilled in the art will recognize that the layer 204 may be patterned using wet etchants, or may be patterned using dry etching techniques such as plasma etching, reactive ion etching, or other etching techniques known to those skilled in the art. Further, for example, as opposed to photoresist masks used in photolithography techniques, other masks formed from various metals, oxides, or nitrides may also be employed as is known to one skilled in the art. Yet further, it may be convenient to use an etchant, whether wet or dry, which provides a higher etch rate for the thin film resistor layer 204 than for the underlying substrate assembly regions, e.g., insulative layer 209. In other words, the etchant would be selective to the insulative layer 209 relative to the thin film resistor layer 204.

As shown in FIG. 3C, after the thin film resistor 205 is formed to the desired configuration, conductive elements 206, 208 may be formed thereon for interconnection of thin film resistor 205 to other circuit elements (not shown). For example, conductive elements 206, 208 may be formed of various conductive materials such as one or more layers of titanium, titanium tungsten, aluminum, aluminum copper, or any other conductive material generally used for interconnection materials in semiconductor fabrication. Such conductive materials are formed and patterned over the thin film resistor 205 as desired and as would be known to one skilled in the art. Preferably, any etching employed to remove conductive material in the patterning of the conductive elements 206, 208 should generally not result in the removal of portions of the thin film resistor 205 as such removal would undesirably thin the resistor 205. In other words, etching or patterning to form conductive elements 206, 208 should be selective to the resistive material used to form thin film resistor 205. As shown in FIG. 3C, the conductive elements used for interconnection of the thin film resistor 205 to other devices, structures, etc. may be formed before deposition of the thin film resistor layer 204. This is generally shown by dashed line conductive elements 213, 215.

One will recognize that various subsequent process steps leading to finished devices, circuits, and/or other apparatus may be performed. For example, deposition of additional insulating materials over resistor surfaces to insulate such layers from other adjacent layers or to provide protection against contamination and handling may be performed.

It will be readily apparent to those skilled in the art from the description herein that variations are possible upon the basic process for forming the various layers and/or structures to be used with thin film resistor layer 204, that variations are possible for the patterning of the thin film resistor layer 204, and that the processes described herein are given for illustration only. As such, various process steps may be required and/or desired in the manufacture of finished integrated circuits, hybrid circuits, or semiconductor devices or other electrical circuits or apparatus utilizing the resistor layer 204 formed according to the present invention.

A variety of different processes may be used to form the thin film resistor layer 204 on the insulative surface 217 of insulative layer 209. For example, chemical vapor deposition, vacuum evaporation, sputtering, reactive sputtering, and/or a combination thereof may be used for forming the thin film resistor layer 204 on insulative surface 217. However, preferably, as described in further detail below, reactive sputtering is employed.

Figure 4:
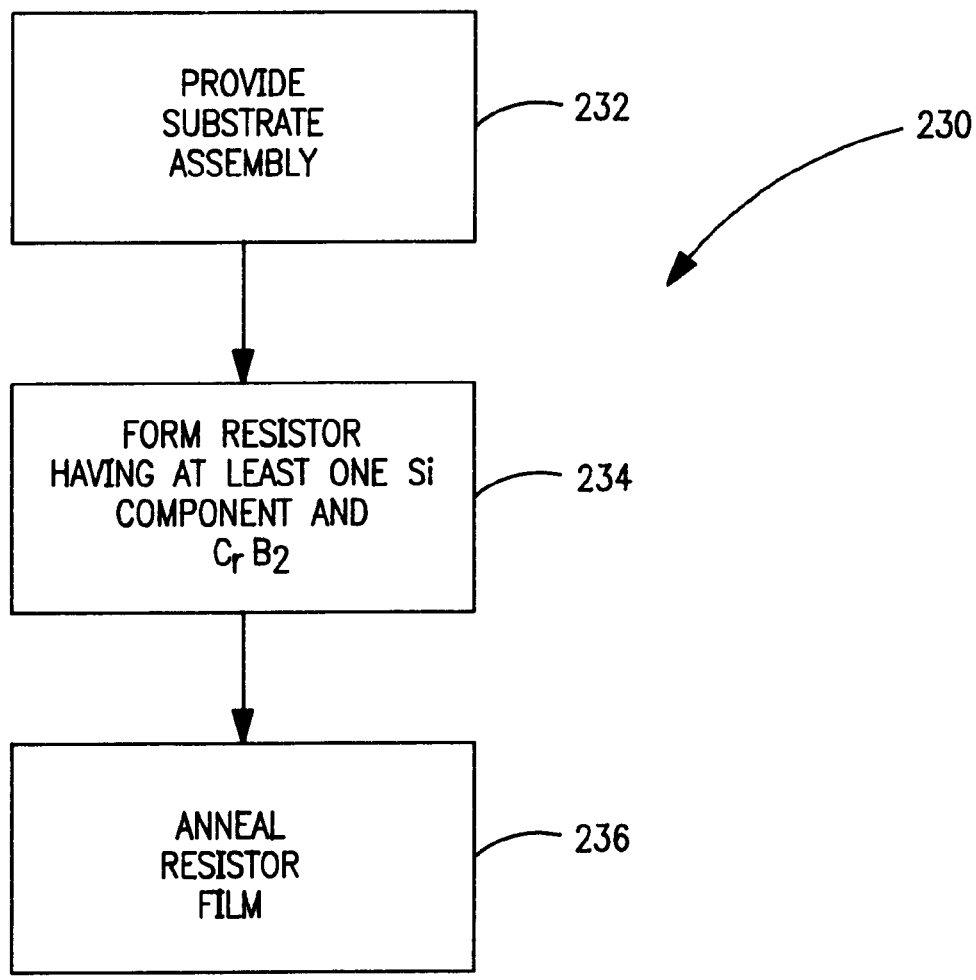
FIG. 4 is a general flow diagram illustrating formation of the thin film resistor of FIGS. 3A–3C according to the present invention.

FIG. 4 is a general flow diagram of a method 230 for forming the thin film resistor layer 204 according to the present invention. First, substrate assembly 202 is provided (Block 232). Thereafter, the thin film resistor layer 204 is formed on the insulative layer 209 of the substrate assembly 202 (Block 234). Preferably, the thin film resistor layer 204 is of a composition of one or more silicon containing components and chromium diboride. After the thin film resistor layer 204 is formed on the substrate assembly 202, the thin film resistor layer 204 is annealed (Block 236).

Figure 5:
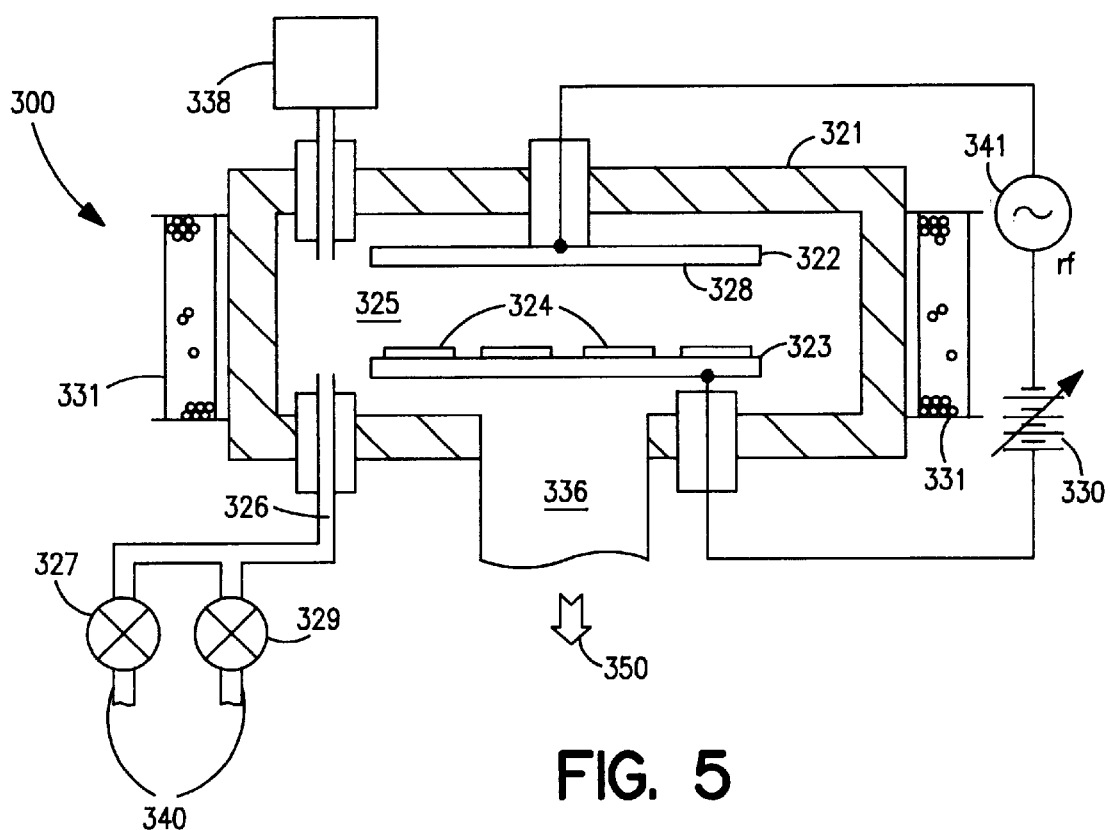
FIG. 5 is a diagram of one illustrative embodiment of a deposition apparatus for use in forming the thin film resistor of FIGS. 3A–3C according to the present invention.

Preferably, the thin film resistor layer 204 is formed by sputtering using one or more nonreactive sputtering gases, e.g., argon. More preferably, the layer 204 is formed by reactive sputtering using at least one reactive gas such as nitrogen, alone or in combination with one or more nonreactive gases. One illustrative sputtering deposition apparatus 300 is shown in FIG. 5. Sputtering deposition apparatus 300 comprises a vacuum chamber 321 containing sputtering target 328 on cathode plate 322 and rotatable wafer support platform 323 adapted to support wafers 324 upon which the thin film resistor layer 204 is formed. The distance between the cathode plate and the wafers 324 shall be referred to herein as the cathode-substrate distance. A gas manifold 326 and flow regulator valves 327, 329 permit a mixture of gases to be introduced into the vacuum chamber 321. The pressure within the vacuum chamber 321 is measured by pressure gauge 338. Power sources 341 and 330, respectively, provide RF and DC energy to the interior of the vacuum chamber 321 to form a gas plasma in the sputtering region 325, i.e., sputtering environment, so as to eject material from sputter target 322. Such energy shall be referred to herein as the sputtering power. A magnetic coil 331 can be optionally used to confine the plasma to the sputtering region or sputtering environment 325 between plates 322 and 323 to increase the efficiency of the sputtering process. General techniques for DC, RF, and/or other reactive sputtering are well known in the art and this illustrative deposition apparatus is given for illustration only and is not meant to be taken as a limitation to the attached claims.

As a generalized example of the process for formation of a thin film resistor layer 204 using the sputter deposition apparatus 300, substrate assemblies 202 (e.g., in the form of silicon wafers 324 having an insulating layer 209 thereon) are loaded on platform 323. Vacuum chamber 321 is evacuated to substantially remove the air present therein. Gases, such as nitrogen and/or argon, can then be continuously provided into the chamber 321 through manifold 326 and flow regulator valves 327, 329 via inlets 340. For example, nitrogen can be continuously provided into chamber 321 through manifold 326 and its flow regulated or adjusted by flow regulating valve 327 to provide a predetermined internal pressure as measured on gauge 338. Further, argon can be continuously provided through manifold 326 and its flow regulated or adjusted by flow regulator 329 to achieve a second, higher fixed predetermined pressure as measured on gauge 338, chosen as desired for sputtering. The pressure in the chamber is referred to herein as the sputtering pressure. Further, it will be recognized that the substrate assembly 202, e.g. wafers 324, are heated to a particular temperature controlled through temperature sensors and heating elements (not shown). This temperature shall be referred to herein as the substrate temperature.

Various sputtering deposition apparatus may be used according to the present invention for forming thin film resistor layer 204. For example, one such sputtering system is available from Sputtered Film Incorporated (Santa Barbara, Calif.) under the trade designation Endeavor 8600 sputtering system. However, other sputtering apparatus may also suitably be used according to the present invention.

Further, it will be recognized that although the sputtering target 328 is shown as a single target in FIG. 5, multiple sputtering targets may be used with multiple power supplies to further provide independent control of the components used to form the thin film resistor layer 204. Further, various techniques such as rotation of the wafers below the sputtering targets may be used to increase uniform coverage of the wafers 324. It should also be noted that the sputter deposition system is dynamic in that gases, such as nitrogen and argon, are continuously being supplied through manifold 326 and removed through vacuum suction 336 as shown by arrow 350.

Preferably, sputtering for achieving a desirable thin film resistor layer 204 having characteristics, e.g., TCR and sheet resistance, falling within the ranges as previously described herein can be achieved under the following process parameters. Preferably, the sputter target has the following composition: about 25 atomic weight percent to about 45 atomic weight percent silicon; about 15 atomic weight percent to about 35 atomic weight percent silicon carbide; and about 20 atomic weight percent to about 60 atomic weight percent chromium diboride.

Further, the various process parameters preferably used for sputter depositing the thin film resistor layer 204 on the substrate assembly 202 include:

Sputtering power: about 300 watts to about 2000 watts

Sputtering pressure: about 2 mTorr to about 8 mTorr

Substrate temperature: about 20° C. to about 500° C.

Nitrogen/Argon ratio: about 0 to about 0.3; nitrogen at a flow rate of about 0 sccm to about 20 sccm; argon at flow rate of about 40 sccm to about 70 sccm.

Cathode-substrate distance: about 50 mm to about 125 mm

Deposition time: about 20 seconds to about 300 seconds

A thin film resistor layer 204 formed under these parameters have characteristics that fall within the ranges as previously described above. For example, the sheet resistance is in a particular range, and the thickness is in the range of 125 Å to about 500 Å. Within the parameters preferably stated above, the various characteristics of the resistor film 204 can be adjusted. For example, the parameters can be adjusted to achieve a zero TCR, the TCR can be adjusted within the range of about −3000 ppm/° C. to about +400 ppm/° C., the sheet resistance can be adjusted from about 0.5 kΩ/sq to about 100 kΩ/sq. Such resistor films can be provided with very good uniformity. For example, the uniformity of sheet resistance may be 2 percent (1σ) within six-inch wafers and from wafer to wafer. Further, the uniformity can be controlled in a reproducible manner such that the uniformity is within 4 percent (1σ) from run to run, i.e., multiple runs of the formation process.

The composition of the thin film resistor layer 204 (primarily based on the sputter target composition) allows the thickness of the layer 204 to be within the range of about 125 Å to about 500 Å, preferably greater than 300 Å, as such a thickness does not reduce the sheet resistance to undesirably low levels. This thickness allows the reactive sputtering process to be easily controlled as there is no need to form an undesirably thin resistor film so as to achieve desirable sheet resistance as is necessary with conventional resistive materials. Resistor films less than 100 Å would make a reactive sputtering process difficult to control for achieving characteristics in the ranges described herein.

After the thin film resistor layer 204 has been formed on the substrate assembly 202 (or alternatively, after it has been patterned), the thin film resistor layer 204 is annealed (Block 236) as shown in FIG. 4. The anneal is required to provide a stable resistive material, i.e., stable with respect to sheet resistance of the material.

The anneal may be performed by various thermal treatment techniques. For example, the anneal may be a furnace anneal, the anneal may be a rapid thermal process (RTP), the anneal may be a rapid thermal nitridation (RTN), or any other annealing technique which would produce satisfactory characteristics for the resistor. Further, the anneal may be performed in multiple steps, at multiple temperatures, for varied or multiple time periods. Any combination of such anneal techniques or steps may be used to result in the desired characteristics for the thin film resistor layer 204.

Preferably, the anneal (Block 236) is a furnace anneal performed at an anneal temperature in the range of about 425° C. to about 600° C. The anneal is preferably performed in an atmosphere of at least nitrogen. More preferably, the anneal is performed in an atmosphere of nitrogen and hydrogen. Preferably, the nitrogen and hydrogen atmosphere is provided to an anneal atmosphere, e.g., a processing chamber, at a nitrogen flow rate of about 8.8 liters/minute to about 12.8 liters/minute and a hydrogen flow rate of 0 liters/minute to about 0.5 liters/minute. Further, preferably, the anneal is performed over a time period of about 20 minutes to about 90 minutes. This anneal time period is the time period the thin film resistor layer 204 is exposed to the temperatures in the ranges given above as opposed to the pull in and pull out time for the furnace anneal.

Generally, the sheet resistance of the thin film resistor layer 204 is primarily controlled in the range as described above by controlling the composition of the sputter target. More preferably, the sheet resistance is controlled by controlling the chromium diboride content of the sputter target and the other components, e.g., the silicon and silicon carbide, of the sputter target relative thereto. For example, the lower the chromium diboride content, the greater the sheet resistance as shown in Example 12.

Figure 7:
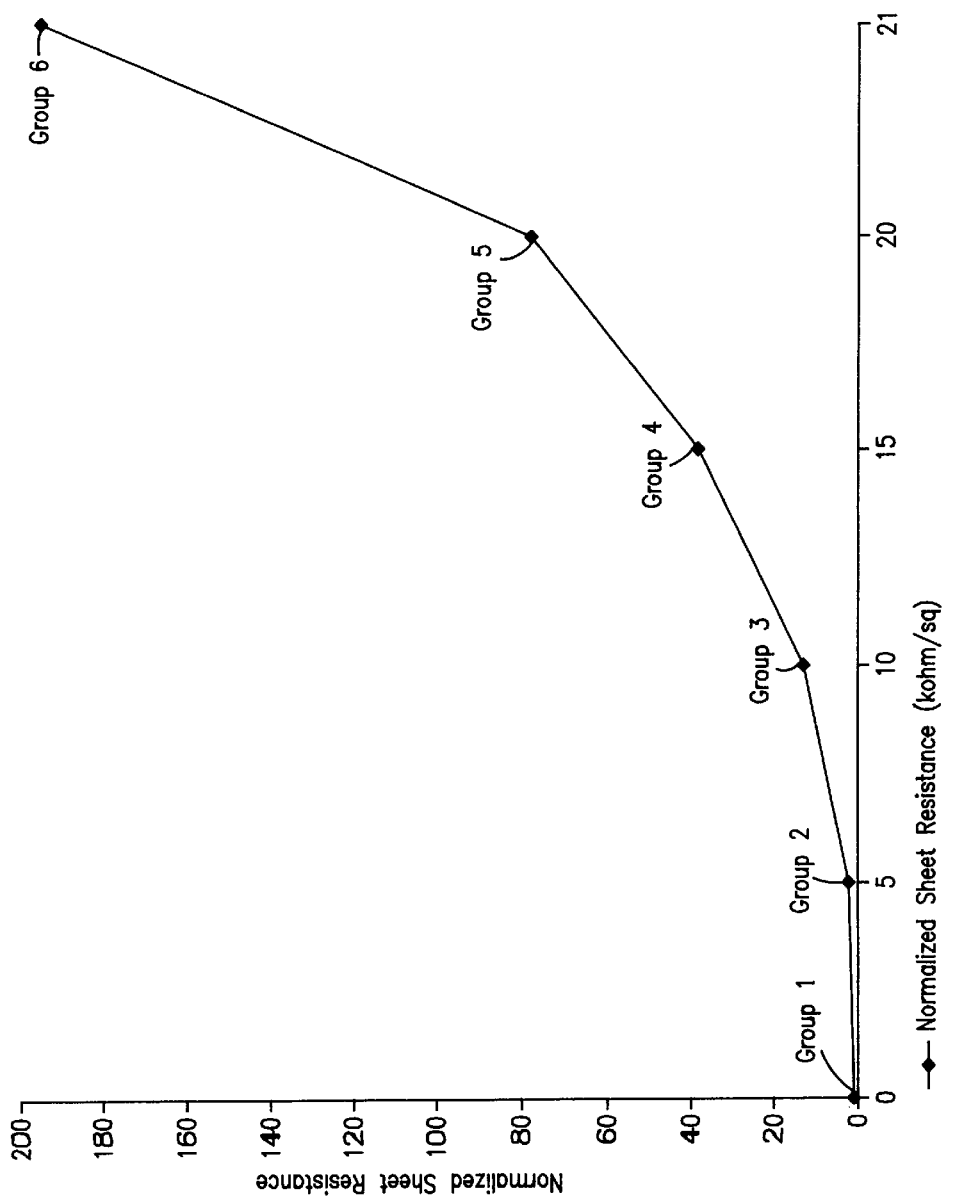
FIGS. 7–11 are graphs showing various characteristics of thin film resistors formed according to the present invention as described with reference to the Examples.
Figure 8:
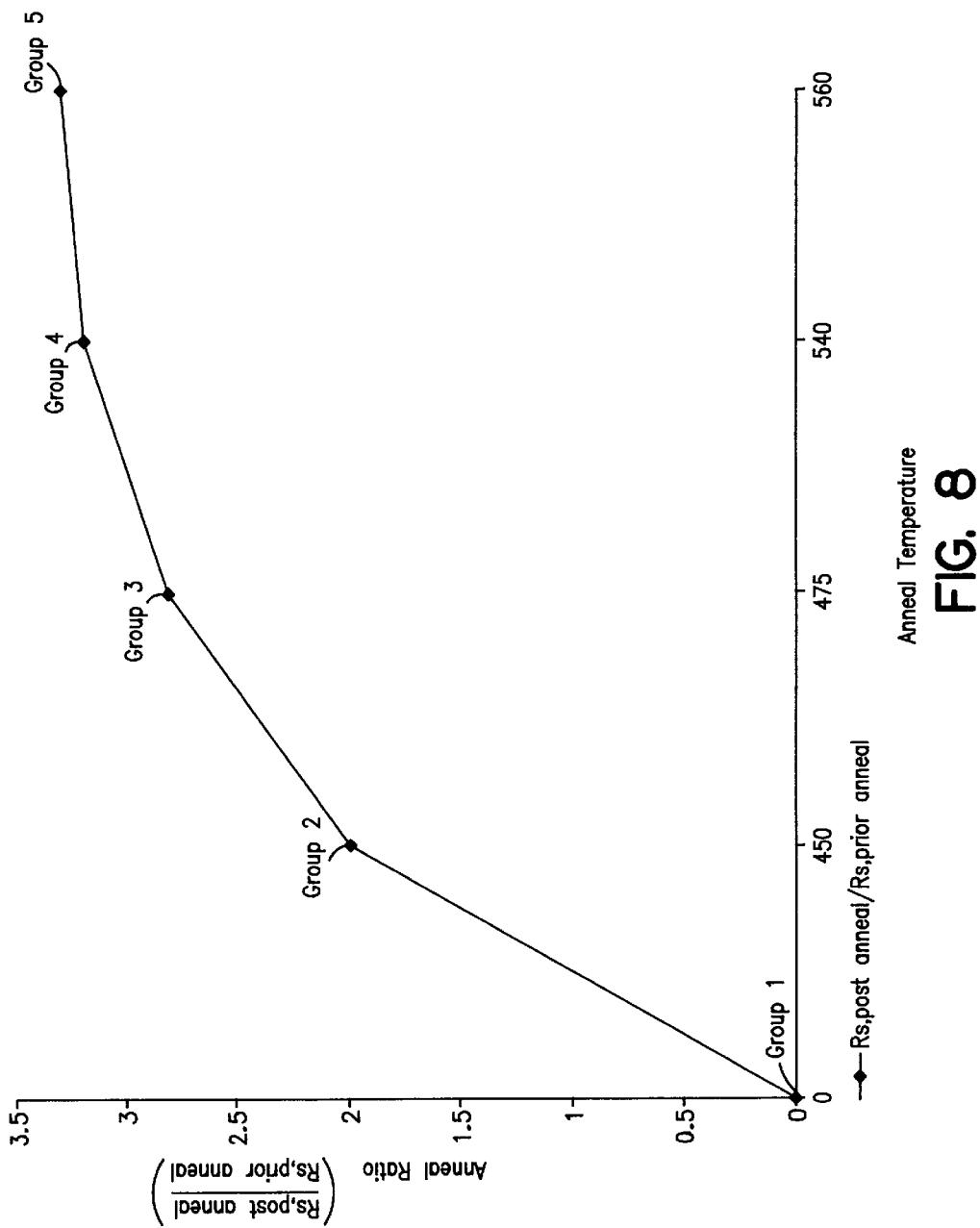

Further, other techniques of controlling the sheet resistance of the thin film resistor layer 204 is by controlling the concentration of nitrogen in the sputtering process as shown in FIG. 7 and the Example 6 described with reference thereto. Yet further, controlling the anneal (Block 236) of the formation process 230 can also be used to control the sheet resistance. For example, the anneal temperature can be varied to control the sheet resistance as shown in FIG. 8 and the Example 7 described with reference thereto, or the anneal atmosphere, e.g., nitrogen versus nitrogen and hydrogen, may be varied to control sheet resistance.

Figure 9:
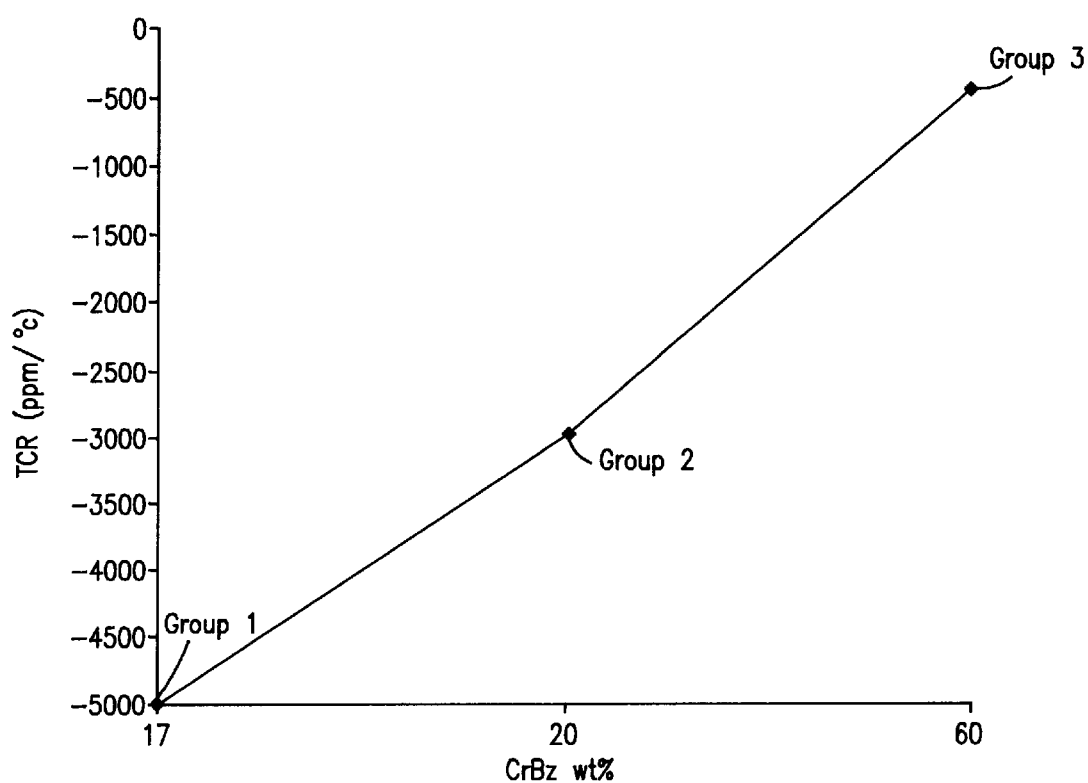
Figure 10:
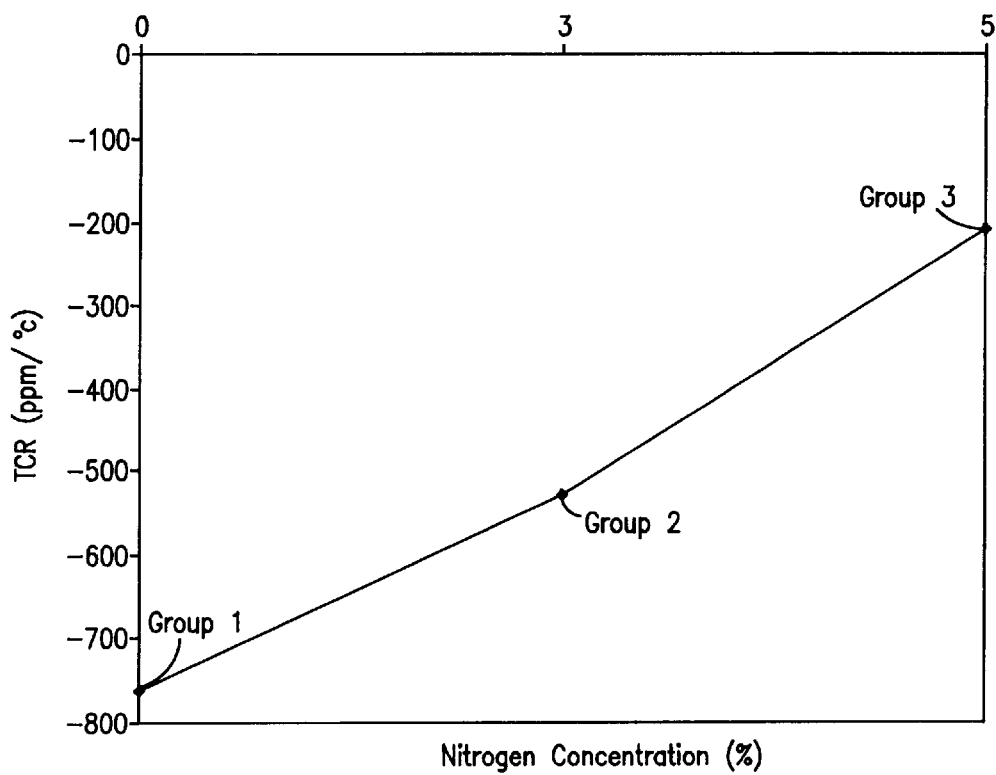
Figure 11:
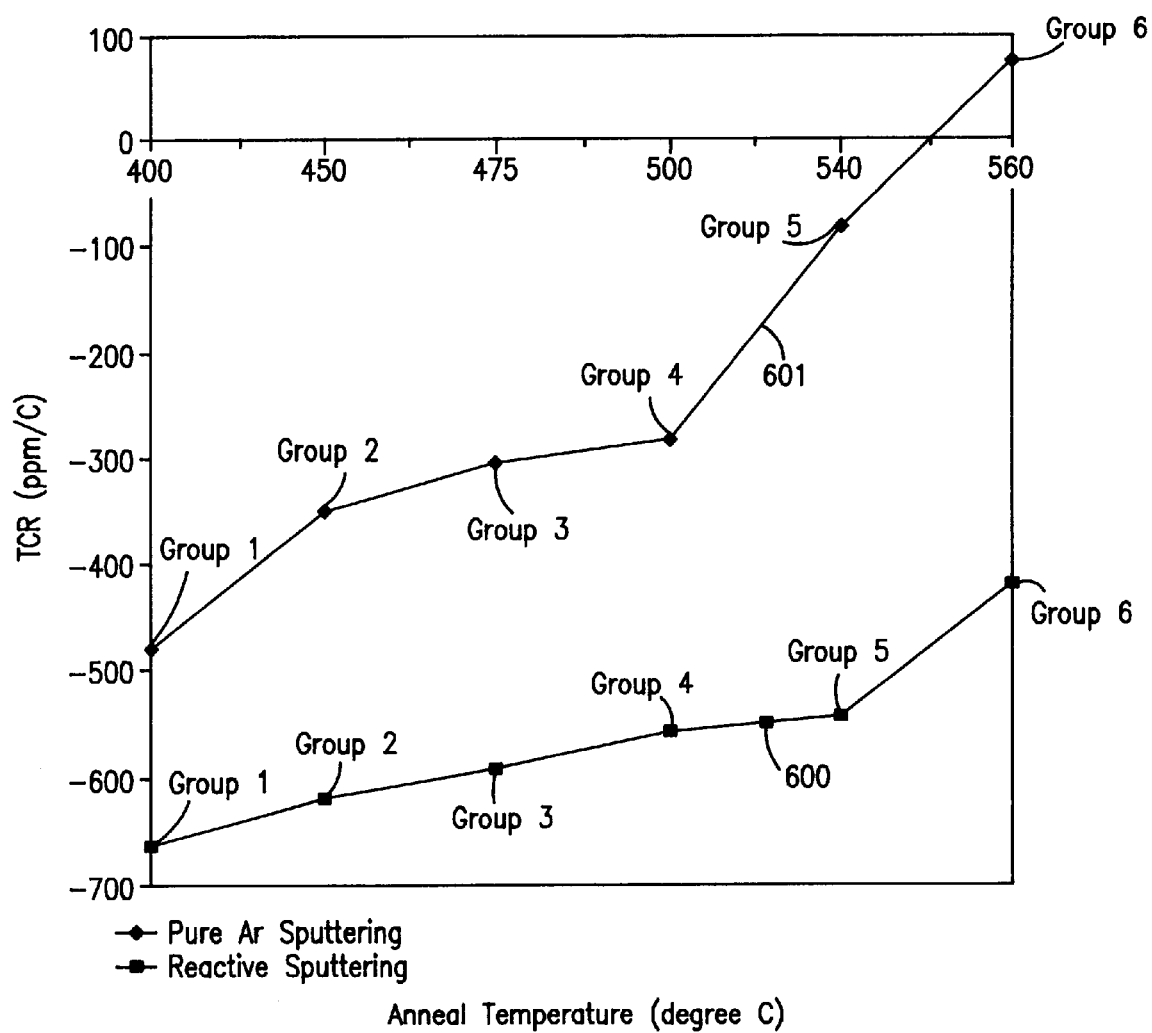

Further, generally, the TCR of the thin film resistor layer 204 can also be adjusted by controlling the sputtering process within the ranges as previously described above. Primarily, the TCR can be controlled through controlling the composition of the sputtering target as shown in FIG. 9 and the Example 8 described with reference thereto. For example, lowering the chromium diboride content of the sputtering target provides for a more negative TCR. Further, by controlling the nitrogen concentration in the process, the TCR can also be adjusted as shown in FIG. 10 and the Example 9 described with reference thereto. For example, increasing the nitrogen in the process will result in a more positive TCR. Likewise, the anneal temperature and the anneal atmosphere can be used to adjust the TCR as shown in FIG. 11 and the Example 10 described with reference thereto. For example, a specific value of anneal temperature can be selected in conjunction with a desired nitrogen or nitrogen/hydrogen atmosphere to obtain a desired TCR.

One skilled in the art will recognize that the interrelationships among the several variable characteristics can be determined by experiment and that a thin film resistor layer 204 having the characteristics in the ranges as described above are possible when the desired combination of sputtering parameters and annealing parameters are selected. Particularly, the TCR and sheet resistance is controlled through controlling the composition of the sputter target, the sputtering environment, the anneal temperature, and the anneal atmosphere as described above.

Figure 6:
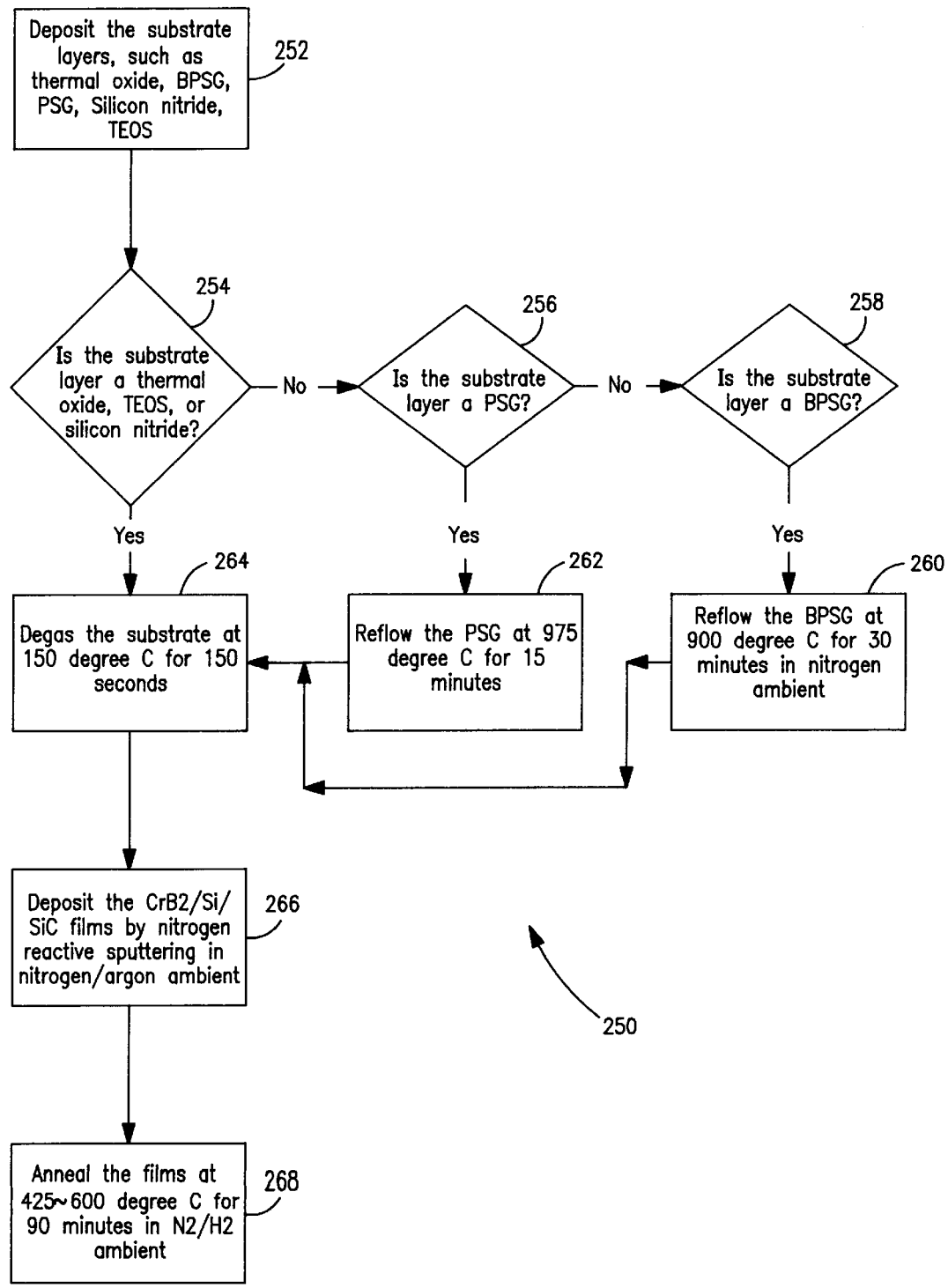
FIG. 6 is a more detailed flow diagram illustrating one embodiment of the method shown in FIG. 4 for forming the thin film resistor on the surface of a substrate assembly according to the present invention.

FIG. 6 shows a flow diagram of one illustrative embodiment of the method 230 for forming a thin film resistor layer 204 as shown in FIG. 4. The illustrative method 250 as shown in FIG. 6 includes, as shown by Block 252, the deposition of substrate assembly layers. For example, such substrate assembly layers may include an insulative layer 209 that is formed of a thermal oxide layer, a BPSG layer, a PSG layer, a silicon nitride layer, a TEOS layer, or any other insulative layer as previously described herein.

Depending upon the type of insulative layer 209 upon which the thin film resistor layer 204 is to be formed (shown in FIG. 6 by a decision being made as indicated by Block 254), varied subsequent process steps are performed. If the insulative layer 209 is a thermal oxide layer, a TEOS layer, or a silicon nitride layer, then the substrate assembly 202 is degassed to remove moisture therefrom. For example, the degassing of the substrate assembly 202 may include heating a substrate to a predetermined temperature for a predetermined period of time. For example, as shown in Block 264, the substrate assembly 202 may be degassed by heating the substrate assembly to 150° C. for about 150 seconds.

If the insulative layer 209 is not a thermal oxide, TEOS, or silicon nitride layer, or in other words, the layer is a deposited oxide layer such as BPSG or PSG, then further processing according to Blocks 256, 258, 260, and 262 are performed. Such steps include at least the step of reflowing the insulative layer 209 to decrease its porosity. In other words, the insulative layer 209 is densified.

As shown in FIG. 6, if the insulative layer 209 is a PSG layer (Block 256), then to densify the insulative layer 209, the PSG is reflowed at a predetermined temperature for a predetermined period of time (Block 262). For example, the reflow process may be performed at a temperature of about 975° C. for about 15 minutes. On the other hand, if the insulative layer 209 of the substrate assembly 202 is a BPSG layer (Block 258), then the reflow process for densifying the layer may be somewhat different, as shown by Block 260. For example, the reflow of the BPSG layer may be performed at a temperature of about 900° C. for about 30 minutes in a nitrogen atmosphere.

After such insulative layers 209, such as BPSG and PSG are reflowed to densify the layers, the substrate assembly 202 is then degassed to remove any moisture therefrom. As indicated above, the degas step shown in Block 264 generally includes heating the substrate assembly to a predetermined temperature for a predetermined period of time adequate to remove substantially all the water vapor present.

After the substrate assembly 202 is degassed to remove the moisture (Block 264), the thin film resistor layer 204 is deposited (Block 266). As shown in Block 266, in this illustrative embodiment, a thin film resistor layer 204 preferably including chromium diboride, silicon, and silicon carbide is deposited from a sputter target containing the same components by a nitrogen reactive sputtering process. The nitrogen reactive sputtering process is preferably performed in a nitrogen/argon atmosphere. It will be recognized that this process may be carried out within the process parameters and ranges previously described herein with reference to FIG. 4 and will not be described in any further detail with reference to FIG. 6.

After the thin film resistor layer 204 is deposited (Block 266), the thin film resistor layer 204 is annealed (Block 268). As shown in Block 268 of FIG. 6, in this particular illustrative embodiment, the layer 204 is annealed at a temperature in the range of 425° C. to about 600° C. for about 90 minutes in a nitrogen and hydrogen atmosphere. One skilled in the art will recognize that the anneal may be performed according to any of the parameters and/or any of the techniques previously described herein for performing anneals of thin film resistor films.

Each of the following Examples 1–4 describing the formation of a thin film resistor were performed using an Endeavor 8600 sputtering system available from Sputtered Film Incorporation (Santa Barbara, Calif.). In each example, a quantity of eight wafers were provided in the Endeavor 8600 sputtering system. Each wafer included an insulative layer of thermally deposited silicon dioxide having a thickness of about 4000 Å. A thin film resistor layer was then deposited on the insulative layer using a sputter target having a composition as given below in each particular example. The formation of the thin film resistor layer was performed according to the parameters given below with respect to each example. The thin film resistor layer was then patterned to a Van der Pauw structure for sheet resistance measurements and TCR measurements. The Van der Pauw structure is well known as documented in the book, Schroeder, D. K., entitled "Semiconductor Material and Device Characterization" (1998).

The patterning was accomplished by coating the resistor layer with photoresist (Shipley SPR3010). The resist was exposed to a combination of g line (436 nm) and h line (405 nm) wavelength and then developed (i.e., using an AIO developer corresponding to the photoresist) leaving exposed regions of the resistor layer. The exposed regions were then dry etched using a combination of $BCl_3$, $Cl_2$, He, and $SF_6$ suitable for removing the desired resistive material. The photoresist was then removed leaving the patterned thin film resistor layer.

Sheet resistance, uniformity of sheet resistance, film thickness, and TCR were then measured or determined. Sheet resistance and uniformity thereof was measured and determined using a Tencor RS75 four point probe. TCR was determined using the HP4156 (with a hot chuck for providing temperature conditions) available from Hewlett Packard. Thickness was determined by SEM cross-section measurements or Tencor P-1 scan Profiler.

EXAMPLE 1

Parameters:

1) Sputtering power: 400 watts.
2) Sputtering pressure: 5 mTorr.
3) Substrate temperature: 25° C.
4) Nitrogen:Argon ratio: 0.05.
5) Cathode-substrate distance: 120 mm.
6) Deposition time: 128 seconds.
7) Anneal temperature: 560° C.
8) Anneal ambient: nitrogen: 10.8 liter/min; hydrogen: 0.5 liter/min.
9) Anneal profile: 20 minutes pull in, 90 minutes soaking, and 20 minutes pull out.
10) 25 atomic weight percent silicon, 15 atomic weight percent silicon carbide, and 60 atomic weight percent chromium diboride.

Results:

Sheet Resistance (Rs): 1.23 kΩ/sq.

Uniformity: (1σ): 2.069%.

Film thickness: 450 Å.

Temperature Coefficient of Resistance (TCR): 0 ppm.

EXAMPLE 2

Parameters:

1) Sputtering power: 900 watts.
2) Sputtering pressure: 3 mTorr.
3) Substrate temperature: 25° C.
4) Nitrogen:Argon ratio: 0.0.
5) Cathode-substrate distance: 120 mm.
6) Deposition time: 35 seconds.
7) Anneal temperature: 600° C.
8) Anneal ambient: nitrogen: 10.8 liter/min; hydrogen: 0.5 liter/min.
9) Anneal profile: 20 minutes pull in, 90 minutes soaking, and 20 minutes pull out.
10) 25 atomic weight percent silicon, 15 atomic weight percent silicon carbide, and 60 atomic weight percent chromium diboride.

Results:

Sheet Resistance (Rs): 828 Ω/sq.

Uniformity (1σ): 1.58%.

Film thickness: 350 Å.

Temperature Coefficient of Resistance (TCR): +400 ppm.

EXAMPLE 3

Parameters:

1) Sputtering power: 900 watts.
2) Sputtering pressure: 5 mTorr.
3) Substrate temperature: 25° C.
4) Nitrogen/Argon ratio: 0.0.
5) Cathode-substrate distance: 120 mm.
6) Deposition time: 120 seconds.
7) Anneal temperature: 600° C.
8) Anneal ambient: nitrogen: 10.8 liter/min; hydrogen: 0.5/liter/min.
9) Anneal profile: 20 minutes pull in, 90 minutes soaking, and 20 minutes pull out.
10) 25 atomic weight percent silicon, 15 atomic weight percent silicon carbide, and 60 atomic weight percent chromium diboride.

Results:

Sheet Resistance (Rs): 1.535 kΩ/sq.

Uniformity (1σ): 1.72%.

Film thickness: 400 Å.

Temperature Coefficient of Resistance (TCR): −767 ppm.

EXAMPLE 4

Parameters:

1) Sputtering power: 1060 watts.
2) Sputtering pressure: 7 mTorr.
3) Substrate temperature: 25° C.
4) Nitrogen/Argon ratio: 0.2.
5) Cathode-substrate distance: 120 mm.
6) Deposition time: 70 seconds.
7) Anneal temperature: 600° C.
8) Anneal ambient: nitrogen: 10.8 liter/min; hydrogen: 0.5 liter/min.
9) Anneal profile: 20 minutes pull in, 90 minutes soaking, and 20 minutes pull out.
10) 45 atomic weight percent silicon, 35 atomic weight percent silicon carbide, and 20 atomic weight percent chromium diboride.

Results:

Sheet Resistance (Rs): 80.4 kΩ/sq.

Uniformity (1σ): 1.92%.

Film thickness: 320 Å.

Temperature Coefficient of Resistance (TCR): −3000 ppm.

Examples 1–4 show the varied characteristics that can be obtained in accordance with the present invention. For example, in Example 2 the TCR=+400 ppm/° C.; in Example 4 the TCR=−3000 ppm/° C.; and in Example 1 the TCR=0 ppm/° C. Further, for example, in Example 4 the Rs is about 80 kΩ/sq while in Example 2 the Rs is about 828 Ω/sq. This wide variety of characteristics are obtainable with suitable uniformity as indicated by the uniformity percentages at least in part due to the ability to use greater thickness for the films as shown by the thickness measurements which for all of the Examples are greater than 300 Å.

EXAMPLE 5

Example 5 describing the formation of thin film resistors was performed using an Endeavor 8600 sputtering system available from Sputtered Film Incorporation (Santa Barbara, Calif.). A quantity of twelve wafers (wafer#'s 13–24) were processed in the Endeavor 8600 sputtering system. Each wafer included an insulative layer of thermally deposited silicon dioxide having a thickness of about 4000 Å. A thin film resistor layer was then deposited on the insulative layer using a sputter target having a composition as described below. Further, the formation of the thin film resistor layer was performed according to the other parameters given below. The thin film resistor layer was then patterned to a Van der Pauw structure for sheet resistance measurements and TCR measurements as described with reference to Examples 1–4. The sheet resistance was measured at 38° C. and 89° C. to determine TCR.

The thin film resistor layers for the wafers were deposited according to the following general parameters:

1. Sputter target composition: Si/SiC/CrB$_2$ (25%/15%/60% atomic weight).
2. Sputtering pressure: 5 mTorr.
3. Sputtering power 900 W.
4. Substrate temperature: 25° C.
5. Cathode-substrate distance: 120 mm
6. Anneal Profile: 90 minutes in N$_2$/H$_2$; nitrogen provided at a flow rate of 10.8 liters/minute; hydrogen provided at a flow rate of 0.5 liters/minute.

The other parameters for forming the thin film resistor layer for the twelve wafers were varied according to the Table 2 below. The Rs and TCR results which occurred as a result of such variation in process are also shown therein.

TABLE 2

| Wafer # | Rs (kΩ/sq) | TCR (ppm/° C.) | Sputter Gas Flow Rate (sccm) | Anneal Temp. (° C.) |
| --- | --- | --- | --- | --- |
| 13 | 1.11 | +90 | Ar = 31 N$_2$ = 0 | 600 |
| 14 | 0.9178 | 0 | Ar = 31 N$_2$ = 0 | 560 |
| 15 | 1.41 | −142 | Ar = 31 N$_2$ = 0 | 540 |
| 16 | 1.228 | −65 | Ar = 31 N$_2$ = 3 | 600 |
| 17 | 1.509 | −93 | Ar = 31 N$_2$ = 3 | 560 |
| 18 | 1.541 | −182 | Ar = 31 N$_2$ = 3 | 540 |

TABLE 2-continued

| Wafer # | Rs (kΩ/sq) | TCR (ppm/° C.) | Sputter Gas Flow Rate (sccm) | Anneal Temp. (° C.) |
|---|---|---|---|---|
| 19 | 1.079 | +167 | Ar = 24 N$_2$ = 0 | 600 |
| 20 | 1.067 | +56 | Ar = 24 N$_2$ = 0 | 560 |
| 21 | 1.405 | −71 | Ar = 24 N$_2$ = 0 | 540 |
| 22 | 1.7 | −106 | Ar = 31 N$_2$ = 6 | 600 |
| 23 | 1.147 | −278 | Ar = 31 N$_2$ = 6 | 560 |
| 24 | 1.079 | −259 | Ar = 31 N$_2$ = 6 | 540 |

From the above Table 2, it can be seen that the TCR can be adjusted between about −300 ppm/° C. to about +200 ppm/° C. by adjusting the anneal temperature and the sputtering environment, i.e., argon and nitrogen flow rates.

EXAMPLE 6

Six groups of eight wafers were processed in a manner substantially the same as described above with reference to Example 1 except that the percentage of nitrogen in the sputtering environment was adjusted for each group as shown in FIG. 7. As shown from FIG. 7, with an increase in the percentage of nitrogen in the sputtering environment, normalized Rs increased significantly. The normalized Rs is normalized by the value of Rs when the percentage of nitrogen in the sputtering environment is zero.

EXAMPLE 7

Five groups of eight wafers were processed in a manner substantially the same as described above with reference to Example 4 except that the anneal temperature was adjusted for each group of wafers as shown in FIG. 8. As shown from FIG. 8, with an increase in anneal temperature, the anneal ratio for Rs (i.e., Rs, post anneal/Rs, prior anneal) also increased significantly.

EXAMPLE 8

A first group of eight wafers were processed in a manner substantially the same as described above with reference to Example 4 except that the CrB$_2$ content of the sputter target was 17 atomic weight % as shown in FIG. 9. A second group of eight wafers were processed in a manner substantially the same as described above with reference to Example 4 except that the CrB$_2$ content of the sputter target was 20 atomic weight % as shown in FIG. 9. A third group of eight wafers were processed in a manner substantially the same as described above with reference to Example 2 except that the CrB$_2$ content of the sputter target was 60 atomic weight % as shown in FIG. 9. Further, as shown from FIG. 9, with a decrease in CrB$_2$ content, the TCR becomes more negative.

EXAMPLE 9

Three groups of eight wafers were processed in a manner substantially the same as described above with reference to Example 1 except that the nitrogen concentration in the sputtering environment was adjusted for each group of wafers as shown in FIG. 10. Further, as shown from FIG. 10, with an increase in nitrogen concentration in the sputtering environment, the TCR became less negative.

EXAMPLE 10

Six groups of eight wafers were processed in a manner substantially the same as described above with reference to Example 2 wherein a pure argon sputtering environment was used. However, the anneal temperature was adjusted for each group of wafers as shown in graph line 601 of FIG. 11. Further, six additional groups of eight wafers were processed in a manner substantially the same as described above with reference to Example 1 wherein a reactive environment including nitrogen was used. However, the anneal temperature was adjusted for each group of wafers as shown in graph line 600 of FIG. 11. Further, as shown from FIG. 11, with an increase in anneal temperature, and with respect to both pure argon sputtering and reactive sputtering, TCR became less negative.

It will be recognized that for the Examples 6–10, many TCR and Rs determinations were made and averaged for the groups of wafers to arrive at the graph values shown.

EXAMPLE 11

Process parameters were controlled to attain wafers having post-annealed thin film resistors having sheet resistances of 1.3 kΩ/sq and 100 kΩ/sq. The wafers having post-annealed thin film resistors of 1.3 kΩ/sq were processed in a manner substantially the same as described with reference to Example 1. The wafers having post-annealed thin film resistors of 100 kΩ/sq were processed in a manner substantially the same as described with reference to Example 4.

The thin film resistors were subjected to X-RAY Photoelectron Spectroscopy (XPS) Surface Analysis to determine the content of the resistors. The following Table 3 shows the results.

TABLE 3

| Element | 1.3 kΩ/sq Atomic Concentration (%) | 100 kΩ/sq Atomic Concentration (%) |
|---|---|---|
| B | 5.2 | 3.7 |
| C | 16.0 | 25.4 |
| N | 1.6 | 1.3 |
| O | 55.4 | 40.2 |
| Si | 16.2 | 27.6 |
| Cr | 5.6 | 1.8 |

It is noted from the above that a significant decrease in Cr is present for a high sheet resistance film versus a low sheet resistance film. Further, it should be noted that the oxygen present may be from diffusion of oxygen into the layer from the thermal oxide layer upon which the resistive layer is formed.

EXAMPLE 12

A groups of eight wafers were processed in substantially the same manner as described with respect to Example 3 above for determination of an average sheet resistivity (ohms/cm) as shown below in Table 4. Further, additional groups of eight wafers were processed in substantially the same manner as described above with respect to Example 4, except that the atomic weight percent of CrB$_2$ was varied for the sputter target to values of 30%, 20%, and 17%.

TABLE 3

| CrB$_2$ - atomic weight %. | Sheet Resistivity (ohm/cm) |
|---|---|
| 60 | 0.0065 |
| 30 | 0.086 |
| 20 | 0.12 |
| 17 | 0.4 |

It should be noted that with decreased CrB$_2$ content the sheet resistivity increases significantly.

All patents and references cited herein are incorporated in their entirety as if each were incorporated separately. This invention has been described with reference to illustrative embodiments and is not meant to be construed in a limiting sense. As described previously, one skilled in the art will recognize that various other illustrative applications may utilize the thin film resistor formed according to the present invention. Various modifications of the illustrative embodiments, as well as additional embodiments of the invention, will be apparent to persons skilled in the art upon reference to this description.

What is claimed is:

1. A method for providing a medical device including at least one resistor, the method comprising the steps of:
   providing a medical device having a housing;
   providing one or more electrical circuits, wherein at least one of the one or more electrical circuits includes a resistor, and further wherein a composition of the resistor includes silicon, silicon carbide, and chromium diboride; and
   enclosing the one or more electrical circuits within the housing of the medical device.

2. The method of claim 1, wherein the composition of the resistor further includes nitrogen.

3. The method of claim 1, wherein the resistor has a thickness in the range of about 125 Å to about 500 Å.

4. The method of claim 3, wherein the resistor has a thickness greater than about 300 Å.

5. The method of claim 1, wherein the resistor has a temperature coefficient of resistance in the range of about −3000 ppm/° C. to about +400 ppm/° C.

6. The method of claim 5, wherein the resistor has a zero temperature coefficient of resistance.

7. The method of claim 1, wherein the resistor has a sheet resistance in the range of about 500 Ω/sq to about 100 kΩ/sq.

8. The method of claim 1, wherein the one or more electrical circuits include an electrical circuit of an implantable device selected from one of a pacemaker, a defibrillator, a pacemaker/cardioverter/defibrillator, a cardioverter/defibrillator, a brain stimulator, a neurostimulator, a muscle stimulator, a gastric stimulator, an implantable monitor, a hemodynamic monitor, and a drug pump.

9. A method for providing a medical device including at least one resistor, the method comprising the steps of:
   providing a medical device having a housing;
   providing one or more electrical circuits, wherein at least one of the one or more electrical circuits includes a resistor, wherein a composition of the resistor includes one or more silicon containing components and chromium diboride, and further wherein the resistor has a thickness in the range of about 125 Å to about 500 Å; and
   enclosing the one or more electrical circuits within the housing of the medical device.

10. The method of claim 9, wherein the composition of the resistor further includes nitrogen.

11. The method of claim 9, wherein the one or more silicon components of the composition of the resistor include silicon and silicon carbide.

12. The method of claim 9, wherein the thickness is greater than 300 Å.

13. The method of claim 9, wherein the resistor has a temperature coefficient of resistance in the range of about −3000 ppm/° C. to about +400 ppm/° C.

14. The method of claim 13, wherein the resistor has a zero temperature coefficient of resistance.

15. The method of claim 9, wherein the resistor has a sheet resistance in the range of about 500 Ω/sq to about 100 kΩ/sq.

16. The method of claim 9, wherein the one or more electrical circuits include an electrical circuit of an implantable device selected from one of a pacemaker, a defibrillator, a pacemaker/cardioverter/defibrillator, a cardioverter/defibrillator, a brain stimulator, a neurostimulator, a muscle stimulator, a gastric stimulator, an implantable monitor, a hemodynamic monitor, and a drug pump.

17. A medical device comprising one or more electrical circuits, wherein at least one of the one or more electrical circuits includes a resistor, and further wherein a composition of the resistor includes silicon, silicon carbide, and chromium diboride.

18. The device of claim 17, wherein the composition of the resistor further includes nitrogen.

19. The device of claim 17, wherein the resistor has a thickness in the range of about 125 Å to about 500 Å.

20. The device of claim 19, wherein the resistor has a thickness greater than about 300 Å.

21. The device of claim 17, wherein the resistor has a temperature coefficient of resistance in the range of about −3000 ppm/° C. to about +400 ppm/° C.

22. The device of claim 21, wherein the resistor has a zero temperature coefficient of resistance.

23. The device of claim 17, wherein the resistor has a sheet resistance in the range of about 500 Ω/sq to about 100 kΩ/sq.

24. The device of claim 17, wherein the one or more electrical circuits include an electrical circuit of an implantable device selected from one of a pacemaker, a defibrillator, a pacemaker/cardioverter/defibrillator, a cardioverter/defibrillator, a brain stimulator, a neurostimulator, a muscle stimulator, a gastric stimulator, an implantable monitor, a hemodynamic monitor, and a drug pump.

25. A medical device comprising one or more electrical circuits, wherein at least one of the one or more electrical circuits includes a resistor, wherein a composition of the resistor includes one or more silicon containing components and chromium diboride, and further wherein the resistor has a thickness in the range of about 125 Å to about 500 Å.

26. The device of claim 25, wherein the composition of the resistor further includes nitrogen.

27. The device of claim 25, wherein the one or more silicon components of the composition of the resistor include silicon and silicon carbide.

28. The device of claim 25, wherein the thickness is greater than 300 Å.

29. The device of claim 25, wherein the resistor has a temperature coefficient of resistance in the range of about −3000 ppm/° C. to about +400 ppm/° C.

30. The device of claim 29, wherein the resistor has a zero temperature coefficient of resistance.

31. The device of claim 25, wherein the resistor has a sheet resistance in the range of about 500 Ω/sq to about 100 kΩ/sq.

32. The device of claim 25, wherein the one or more electrical circuits include an electrical circuit of an implantable device selected from one of a pacemaker, a defibrillator, a pacemaker/cardioverter/defibrillator, a cardioverter/defibrillator, a brain stimulator, a neurostimulator, a muscle stimulator, a gastric stimulator, an implantable monitor, a hemodynamic monitor, and a drug pump.

33. A resistor comprising silicon, silicon carbide, and chromium diboride.

34. The resistor of claim 33, wherein the resistor further includes nitrogen.

35. The resistor of claim 34, wherein the resistor further includes hydrogen.

36. The resistor of claim 34, wherein the resistor has a temperature coefficient of resistance in the range of about −3000 ppm/° C. to about +400 ppm/° C.

37. The resistor of claim 36, wherein the resistor has a zero temperature coefficient of resistance.

38. The resistor of claim 33, wherein the resistor has a thickness in the range of about 125 Å to about 500 Å.

39. The resistor of claim 38, wherein the resistor has a thickness greater than about 300 Å.

40. The resistor of claim 33, wherein the resistor has a sheet resistance in the range of about 500 Ω/sq to about 100 kΩ/sq.

41. A resistor comprising one or more silicon containing components and chromium diboride, wherein the resistor has a thickness in the range of about 125 Å to about 500 Å.

42. The resistor of claim 41, wherein the resistor further comprises nitrogen.

43. The resistor of claim 41, wherein the one or more silicon containing components of the composition of the resistor include silicon and silicon carbide.

44. The resistor of claim 41, wherein the thickness of the resistor is greater than about 300 Å.

45. The resistor of claim 41, wherein the resistor has a temperature coefficient of resistance in the range of about −3000 ppm/° C. to about +400 ppm/° C.

46. The resistor of claim 41, wherein the resistor has a zero temperature coefficient of resistance.

47. The resistor of claim 41, wherein the resistor has a sheet resistance in the range of about 500 Ω/sq to about 100 kΩ/sq.

48. A method of forming a resistor on a surface, the method comprising the steps of:

providing a sputter target, wherein the sputter target has a composition including one or more silicon containing components and chromium diboride; and sputter depositing a resistive material on the surface to a thickness in the range of about 125 Å to about 500 Å using a nitrogen containing sputter gas and the sputter target.

49. The method of claim 48, wherein the method further includes the step of annealing the sputter deposited resistive material in an anneal atmosphere.

50. The method of claim 49, wherein the step of annealing the sputter deposited resistive material includes annealing the deposited resistive material in an anneal atmosphere comprising at least nitrogen.

51. The method of claim 50, wherein the step of annealing the deposited resistive material in an anneal atmosphere comprising at least nitrogen includes annealing the deposited resistive material in an anneal atmosphere comprising nitrogen and hydrogen.

52. The method of claim 49, wherein the step of sputter depositing the resistive material includes adjusting the temperature coefficient of resistance of the resistive material in a range of about −3000 ppm/° C. to about +400 ppm/° C. by controlling the anneal atmosphere.

53. The method of claim 49, wherein the step of sputter depositing the resistive material includes adjusting the sheet resistance of the resistive material in a range of about 500 Ω/sq to about 100 kΩ/sq by controlling the anneal atmosphere.

54. The method of claim 49, wherein the step of annealing the deposited resistive material includes annealing the deposited resistive material in at an anneal temperature in the range of about 425° C. to about 600° C.

55. The method of claim 54, wherein the step of sputter depositing the resistive material includes adjusting the temperature coefficient of resistance of the resistive material in a range of about −3000 ppm/° C. to about +400 ppm/° C. by controlling the anneal temperature.

56. The method of claim 54, wherein the step of sputter depositing the resistive material includes adjusting the sheet resistance of the resistive material in a range of about 500 Ω/sq to about 100 kΩ/sq by controlling the anneal temperature.

57. The method of claim 48, wherein the composition of the sputter target includes the one or more silicon containing components at an atomic weight percent in the range of about 40 percent to about 80 percent and the chromium diboride at an atomic weight percent of about 20 percent to about 60 percent.

58. The method of claim 57, wherein the one or more silicon containing components of the sputter target include silicon and silicon carbide.

59. The method of claim 58, wherein the one or more silicon containing components of the sputter target include the silicon at an atomic weight percent in the range of about 25 percent to about 45 percent and the silicon carbide at an atomic weight percent of about 15 percent to about 35 percent.

60. The method of claim 48, wherein the step of sputter depositing the resistive material on the surface includes sputter depositing the resistive material on the surface in a sputter atmosphere of a nitrogen and argon containing sputter gas.

61. The method of claim 60, wherein the nitrogen and argon containing sputter gas includes a nitrogen:argon sputter gas at a ratio in the range of about 0 to about 0.3.

62. The method of claim 60, wherein the step of sputter depositing the resistive material includes adjusting the temperature coefficient of resistance of the resistive material in a range of about −3000 ppm/° C. to about +400 ppm/° C. by controlling the sputtering atmosphere.

63. The method of claim 60, wherein the step of sputter depositing the resistive material includes adjusting the sheet resistance of the resistor in a range of about 500 Ω/sq to about 100 kΩ/sq by controlling the sputtering atmosphere.

64. The method of claim 48, wherein the method further includes the step of patterning the resistive material.

65. A method of forming a resistor, the method comprising the steps of:

providing a surface;

exposing the surface to one or more sources of silicon, silicon carbide, chromium diboride, and nitrogen to form a resistive material on the surface; and annealing the resistive material.

66. The method of claim 65, wherein exposing the surface to one or more sources of silicon, silicon carbide, chromium diboride, and nitrogen includes:

providing a sputter target in a chamber, wherein the sputter target has a composition including silicon, silicon carbide, and chromium diboride; and sputter depositing the resistive material on the surface using the sputter target and a sputter gas.

67. The method of claim 66, wherein the composition of the sputter target includes the silicon at an atomic weight percent in the range of about 25 percent to about 45 percent, the silicon carbide at an atomic weight percent of about 15 to about 35 percent, and the chromium diboride at an atomic weight percent of about 20 percent to about 60 percent.

68. The method of claim 66, wherein the step of exposing the surface to one or more sources of silicon, silicon carbide, chromium diboride, and nitrogen to form a resistive material on the substrate surface includes depositing the resistive material to a thickness in the range of about 125 Å to about 500 Å.

69. The method of claim 66, wherein the step of annealing the resistive material includes annealing the resistive material in an anneal atmosphere comprising at least nitrogen.

70. The method of claim 69, wherein the step of annealing the resistive material in an anneal atmosphere comprising at least nitrogen includes annealing the resistive material in an anneal atmosphere comprising nitrogen and hydrogen.

71. The method of claim 70, wherein the step of sputter depositing the resistive material includes adjusting the temperature coefficient of resistance of the resistive material in a range of about −3000 ppm/° C. to about +400 ppm/° C. by controlling the anneal atmosphere.

72. The method of claim 70, wherein the step of sputter depositing the resistive material includes adjusting the sheet resistance of the resistive material in a range of about 500 Ω/sq to about 100 kΩ/sq by controlling the anneal atmosphere.

73. The method of claim 66, wherein the step of annealing the resistive material includes annealing the deposited resistive material at an anneal temperature in the range of about 425° C. to about 600° C.

74. The method of claim 73, wherein the step of sputter depositing the resistive material includes adjusting the temperature coefficient of resistance of the resistive material in a range of about −3000 ppm/° C. to about +400 ppm/° C. by controlling the anneal temperature.

75. The method of claim 73, wherein the step of sputter depositing the resistive material includes adjusting the sheet resistance of the resistive material in a range of about 500 Ω/sq to about 100 kΩ/sq by controlling the anneal temperature.

76. The method of claim 66, wherein the step of sputter depositing the resistive material on the surface includes sputter depositing the resistive material on the surface in a sputter atmosphere of at least nitrogen.

77. The method of claim 76, wherein the step of sputter depositing the resistive material on the surface includes sputter depositing the resistive material on the surface in a sputter atmosphere of nitrogen and argon, and further wherein the nitrogen and argon containing sputter gas includes a nitrogen:argon sputter gas at a ratio in the range of about 0 to about 0.3.

78. The method of claim 76, wherein the step of sputter depositing the resistive material includes adjusting the temperature coefficient of resistance of the resistive material in a range of about −3000 ppm/° C. to about +400 ppm/° C. by controlling the sputtering atmosphere.

79. The method of claim 76, wherein the step of sputter depositing the resistive material includes adjusting the sheet resistance of the resistor in a range of about 500 Ω/sq to about 100 kΩ/sq by controlling the sputtering atmosphere.

80. The method of claim 65, wherein the method further includes the step of patterning the resistive material.

\* \* \* \* \*